(12) United States Patent
Fisher et al.

(10) Patent No.: US 7,704,237 B2
(45) Date of Patent: Apr. 27, 2010

(54) MEDICATION DISPENSING APPARATUS CONFIGURED FOR ROTATE TO PRIME AND PULL/PUSH TO INJECT FUNCTIONALITY

(75) Inventors: Mark James Fisher, Highland Park, IL (US); Traci Jo Barron, Chicago, IL (US); Scott Alan Massing, Chicago, IL (US); Iain Roberts, Chicago, IL (US)

(73) Assignee: Eli Lilly and Company, Indianapolis, IN (US)

( * ) Notice: Subject to any disclaimer, the term of this patent is extended or adjusted under 35 U.S.C. 154(b) by 560 days.

(21) Appl. No.: 11/677,754

(22) Filed: Feb. 22, 2007

(65) Prior Publication Data

US 2007/0142789 A1 Jun. 21, 2007

Related U.S. Application Data

(62) Division of application No. 10/483,976, filed as application No. PCT/US02/19815 on Jul. 15, 2002, now abandoned.

(60) Provisional application No. 60/305,733, filed on Jul. 16, 2001, provisional application No. 60/354,237, filed on Feb. 4, 2002.

(51) Int. Cl.
*A61M 5/00* (2006.01)
*A61M 5/315* (2006.01)
(52) U.S. Cl. ...................... 604/208; 604/224
(58) Field of Classification Search ......... 604/207–211, 604/218, 224, 246
See application file for complete search history.

(56) References Cited

U.S. PATENT DOCUMENTS

| | | | |
|---|---|---|---|
| 4,592,745 A | 6/1986 | Rex et al. | |
| 4,865,591 A | 9/1989 | Sams | |
| 5,092,842 A | 3/1992 | Bechtold et al. | |
| 5,114,406 A | 5/1992 | Gabriel et al. | |
| 5,226,895 A | 7/1993 | Harris | |
| 5,300,041 A | 4/1994 | Haber et al. | |
| 5,383,865 A | 1/1995 | Michel | |
| 5,480,387 A | 1/1996 | Gabriel et al. | |
| 5,496,293 A | 3/1996 | Huggenberger | |
| 5,514,097 A | 5/1996 | Knauer | |
| 5,591,136 A | 1/1997 | Gabriel | |
| 5,593,388 A | 1/1997 | Phillips | |
| 5,593,390 A | 1/1997 | Castellano et al. | |
| 5,599,314 A | 2/1997 | Neill | |

(Continued)

FOREIGN PATENT DOCUMENTS

EP 1 000 631 10/1997

(Continued)

*Primary Examiner*—Kevin C Sirmons
*Assistant Examiner*—Andrew M Gilbert
(74) *Attorney, Agent, or Firm*—Edward J. Prein

(57) ABSTRACT

A medication dispensing apparatus having a manually operable plunger axially shiftable relative to the apparatus housing. The plunger is pullable relative to the housing in a proximal direction to cock the apparatus, and when the plunger is then manually pushed back toward the housing, a piston within a medicine container of the apparatus is shifted to force medication from a needle assembly at the distal end of the apparatus. The medication dispensing apparatus also includes a priming mechanism which is operated by rotating an externally accessible driver portion to prime the apparatus for use, which priming can be performed whether or not the apparatus is in a cocked state.

19 Claims, 16 Drawing Sheets

U.S. PATENT DOCUMENTS

| | | |
|---|---|---|
| 5,637,094 A | 6/1997 | Stewart et al. |
| 5,688,251 A | 11/1997 | Chanoch |
| 5,807,346 A | 9/1998 | Frezza |
| 5,820,602 A | 10/1998 | Kovelman et al. |
| 5,961,495 A * | 10/1999 | Walters et al. ............ 604/208 |
| 6,048,336 A | 4/2000 | Gabriel |
| 6,053,893 A | 4/2000 | Bucher |
| 6,090,080 A | 7/2000 | Jost et al. |
| 6,096,010 A | 8/2000 | Walters et al. |
| 6,110,149 A | 8/2000 | Klitgaard et al. |
| 6,221,053 B1 | 4/2001 | Walters et al. |
| 6,228,067 B1 | 5/2001 | Gabriel |
| 6,241,709 B1 | 6/2001 | Bechtold et al. |
| 6,277,101 B1 | 8/2001 | Kirchhofer et al. |
| 6,699,224 B2 | 3/2004 | Kirchhofer et al. |
| 6,936,032 B1 | 8/2005 | Bush et al. |
| 2001/0051792 A1 | 12/2001 | Kirchhofer et al. |
| 2002/0173752 A1 | 11/2002 | Polzin |

FOREIGN PATENT DOCUMENTS

| | | |
|---|---|---|
| EP | 0 937 472 | 2/1999 |
| EP | 0 937 477 | 8/1999 |
| WO | WO 00/41752 | 7/2000 |
| WO | WO 01/10484 | 2/2001 |
| WO | WO 01/60311 | 8/2001 |

* cited by examiner

MEDICATION DISPENSING APPARATUS CONFIGURED FOR ROTATE TO PRIME AND PULL/PUSH TO INJECT FUNCTIONALITY

This application is a divisional of Ser. No. 10/483,976 filed Jan. 9, 2004, now abandoned which was a §371 national application of PCT/US02/19815 filed Jul. 15, 2002, which claims the benefit of Provisional Application Nos. 60/305,733 filed Jul. 16, 2001, and 60/354,237 filed Feb. 4, 2002.

BACKGROUND OF THE INVENTION

The present invention pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable pens, after a pen has been utilized to exhaust the supply of medication within the cartridge, the entire pen is discarded by a user, who then begins using a new replacement pen. In reusable pens, after a pen has been utilized to exhaust the supply of medication within the cartridge, the pen is disassembled to allow replacement of the spent cartridge with a fresh cartridge, and then the pen is reassembled for it subsequent use.

For an injector pen to be used optimally, just prior to using the pen to inject oneself with medicine, a user should prime that pen. During priming, the pen is operated to shift the cartridge piston a sufficient distance to force any air from the cartridge and to shift the cadge piston a sufficient distance to force any air from the cartridge and needle and cause medicine to reach the exposed distal or forward tip of the needle, such that the subsequent injecting use of the pen in fact delivers the volume of medicine the pen is arranged to deliver. Some users, however, fail to so prime the pen, resulting in an injecting of less medicine than presumably intended by the user.

One possible explanation for the failure to prime is that the design of most injector pens does not assist the user in conceptually distinguishing a priming step from a dose injecting step. In particular, the priming step typically involves setting the pen to deliver a small dose, operating the pen without injecting the user but otherwise in the same manner as would be performed during user injection, and then repeating these steps if necessary, until priming has been accomplished. Then, during the dose injecting step, the dose is actually set in exactly the same way as in the priming step but typically in a larger quantity, and then the pen is used to inject the medicine into the user.

U.S. Pat. No. 5,961,495 discloses an injection pen in which the priming control mechanism is by outward appearances distinct from the mechanism used to actually set and then inject the selected dose into a user. Dose setting and injection is accomplished with a dose knob at the proximal end of the pen housing. The dose knob is rotatable to set one of a number of dose quantities which are possible to select. Injection of the set dose is accomplished by pulling out the dose knob, and then pushing the knob in after the pen has been manipulated such that its injection needle has penetrated the user's skin. The priming mechanism utilizes a manually operable priming control sleeve that is spaced from the dose knob. The priming control sleeve is connected to the internal drive mechanism of the pen such that the sleeve can be manually rotationally pivoted back and forth as necessary to prime the pen in anticipation of the injection operation. While perhaps functional, this design is not without its shortcomings. For one thing, the adjustability in the setting of the dose to be injected results in a relatively complicated pen design, which may undesirably increase the cost of manufacture and assembly of the pen. The back and forth ratcheting action of the priming control sleeve possibly required to achieve pen priming also may be confusing or not intuitive to some users, who might therefore fail to prime the pen completely. In addition, the dose setting capacity of the pen is a potential source of dosing errors as the user who intends to inject the same quantity of medicine as injected the last time the pen was used may fail to pay proper attention to the dose actually set, which set dose may be different than what was set previously as a result of an inadvertent switching since the prior use.

Thus, it would be desirable to provide an apparatus that overcomes these and other shortcomings of the prior art.

BRIEF SUMMARY OF THE INVENTION

In one form thereof, the present invention provides a medication dispensing apparatus including a housing, a fluid container mounted to the housing and defining a medicine-filled reservoir, a needle assembly removably attached to a distal end of the fluid container to have an injection needle of the needle assembly in flow communication with the reservoir, and a drive mechanism for dispensing a dose of medicine from the reservoir through the injection needle, which drive mechanism includes a plunger that is manually pullable relative to the housing in a proximal direction to shift the apparatus from a ready state to a cocked state, and which is manually pushable relative to the housing in a distal direction to force medicine out the injection needle while returning the apparatus from the cocked state to the ready state. The apparatus includes a priming mechanism for priming the injection needle with medicine from the reservoir, which priming mechanism includes a drive portion external to the housing to be manually rotatable relative to the housing, The apparatus further includes a rotation controlling mechanism that manual rotation of the priming mechanism drive portion in a first direction and as far as necessary to achieve priming, and that prevents manual rotation of the priming mechanism drive portion in a direction opposite to the first direction.

In another form thereof, the present invention provides a medication dispensing apparatus including a housing, a fluid container mounted to the housing and defining a medicine-filled reservoir, a needle assembly removably attached to a distal end of the fluid container to have an injection needle of the needle assembly in flow communication with the reservoir, a drive mechanism for dispensing a dose of medicine from the reservoir through the injection needle, which drive mechanism includes a plunger that is manually pullable relative to the housing in a proximal direction to shift the apparatus from a ready state to a cocked state, and which is manually pushable relative to the housing in a distal direction to force medicine out the injection needle while returning the apparatus from the cocked state to the ready state. The apparatus includes a priming mechanism for priming the injection needle with medicine from the reservoir by manually rotating an element other than the plunger, and the priming mechanism is operable to effect priming whether the apparatus is in the cocked state or the ready state, and without altering the dose to be dispensed by the drive mechanism if the apparatus is in the cocked state.

In another form thereof, the present invention provides a medication dispensing apparatus including a housing, a fluid container mounted to the housing and defining a medicine-filled reservoir with a movable piston at a proximal end, a needle assembly removably attached to a distal end of the fluid container to have an injection needle of the needle assembly in flow communication with the reservoir, a drive member axially extending within the housing and movable distally to advance the movable piston toward the injection needle, which drive member, along an axial cross-section, has a series of axially spaced projections, a follower portion engagable with the projections and having a resilient construction, and a plunger operably connected to the follower portion and manually pullable in a proximal direction to shift the plunger from a first position to a second position, and manually pushable in a distal direction to shift the plunger from the second position to the first position. The follower portion is axially shiftable by movement of the plunger in the proximal and distal directions. The follower portion bends radially outward and axially slides over at least one projection of the drive member when the plunger is pulled proximally to shift from the first position to the second position, and the follower portion, by abutment with a projection of the drive member over which the follower portion previously slid, advances the drive member distally when the plunger is pushed distally from the second position to the first position. The apparatus further includes a priming driver operably connected to the drive member and including a drive portion external to the housing which is manually rotatable independently of the plunger to axially advance the drive member to prime the injection needle with medicine from the reservoir.

In still another form thereof, the present invention provides a medication dispensing apparatus including a housing, a fluid container mounted to the housing and defining a medicine-filled reservoir with a movable piston at one end and an outlet at the other end, a drive screw with external threading and axially extending within the housing and movable distally to advance the movable piston toward the outlet, at least one anti-rotation member operably engaging the drive screw to prevent rotation of the drive screw within the housing, and a priming driver axially retained relative to the housing and having a first portion and a second portion, the first portion internal to the housing and in threaded engagement with the drive screw, the second portion external to the housing to be manually rotatable, whereby rotation of the second portion rotates the first portion to force the drive screw to translate distally. The apparatus further includes a follower and a plunger. The follower is axially movable relative to the priming driver and rotatably fixed thereto, and includes a portion internal to the housing and in threaded engagement with the drive screw. The plunger is axially movable relative to the housing between a distal position and a proximal position. The plunger includes a manually graspable grip portion which is pullable proximally to move the plunger from the distal position to the proximal position, and the plunger is connected to the follower to allow relative rotation therebetween and to shift the follower axially when the plunger moves back and forth between the distal and proximal positions. Each of the follower portion and the priming driver first portion has a resilient construction, whereby when the plunger is pulled from the distal position to the proximal position to shift the follower proximally, the follower portion slides over the threading of the drive screw that is being axially retained by engagement with the priming driver first portion, and whereby when the plunger is pushed from the proximal position to the distal position to shift the follower distally, the priming driver first portion slides over the threading of the drive screw that is being axially advanced by engagement with the follower portion.

One advantage of the present invention is that a medication dispensing apparatus can be provided which is to be primed in a fundamentally different manner than the manner by which it is to be used to inject a dose of medicine, thereby providing a user with an aid to remembering to prime the apparatus prior to injection.

Another advantage of the present invention is that a medication dispensing apparatus can be provided which can be easily primed using a manually rotatable element, and easily used to inject a dose by manually pulling out and then pushing in a plunger.

Another advantage of the present invention is that a medication dispensing apparatus can be provided which delivers a fixed dose, and therefore does not require any dose setting feature which could be accidentally altered prior to use to cause an incorrect dose to be delivered.

Another advantage of the present invention is that a medication dispensing apparatus can be provided which can be made from a small number of parts so as to be relatively inexpensive to produce, and thereby more justifiably disposable after its medication contents are exhausted.

Still another advantage of the present invention is that a medication dispensing apparatus can be provided which due to it being made from a limited number of parts, lacks any large stack up of manufacturing tolerances which could adversely impact the dose accuracy.

Still another advantage of the present invention is that a medication dispensing apparatus can be provided which can be primed even after having been cocked for injection, thereby avoiding any wasting of medication associated with having to uncock a cocked apparatus for priming purposes.

Still another advantage of the present invention is that a medication dispensing apparatus can be provided in which even if its priming mechanism is used after the apparatus is cocked for injection, the amount of medication to be delivered by operation of the cocked apparatus is not altered.

Yet another advantage of the present invention is that a medication dispensing apparatus can be provided which can be primed by manually and continuously rotating a priming sleeve as far as necessary, including one or more complete revolutions, which priming is highly adjustable and does not waste a sizeable amount of medication.

Yet another advantage of the present invention is that a medication dispensing apparatus can be provided with an uncomplicated and computer design that contributes to a small axial profile and diameter of the apparatus.

Yet another advantage of the present invention is that a medication dispensing apparatus can be provided which is accurate, and simpler in design and operation than many existing devices.

Yet another advantage of the present invention is that a medication dispensing apparatus can be provided with a drive member that can be reset and a medication cartridge that can be replaced, thereby allowing the apparatus to be reused rather than discarded when its initial medication cartridge is spent.

Yet another advantage of the present invention is that a medication dispensing apparatus can be provided with a drive member that is automatically axially unlocked so as to allow reset when a medication cartridge is being replaced.

Yet another advantage of the present invention is that a medication dispensing apparatus can be provided with a drive member that during the final stage of its axial reset is automatically shifted to its final position so as to provide feedback to the user that the drive member has been reset properly.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein.

Figure 1:
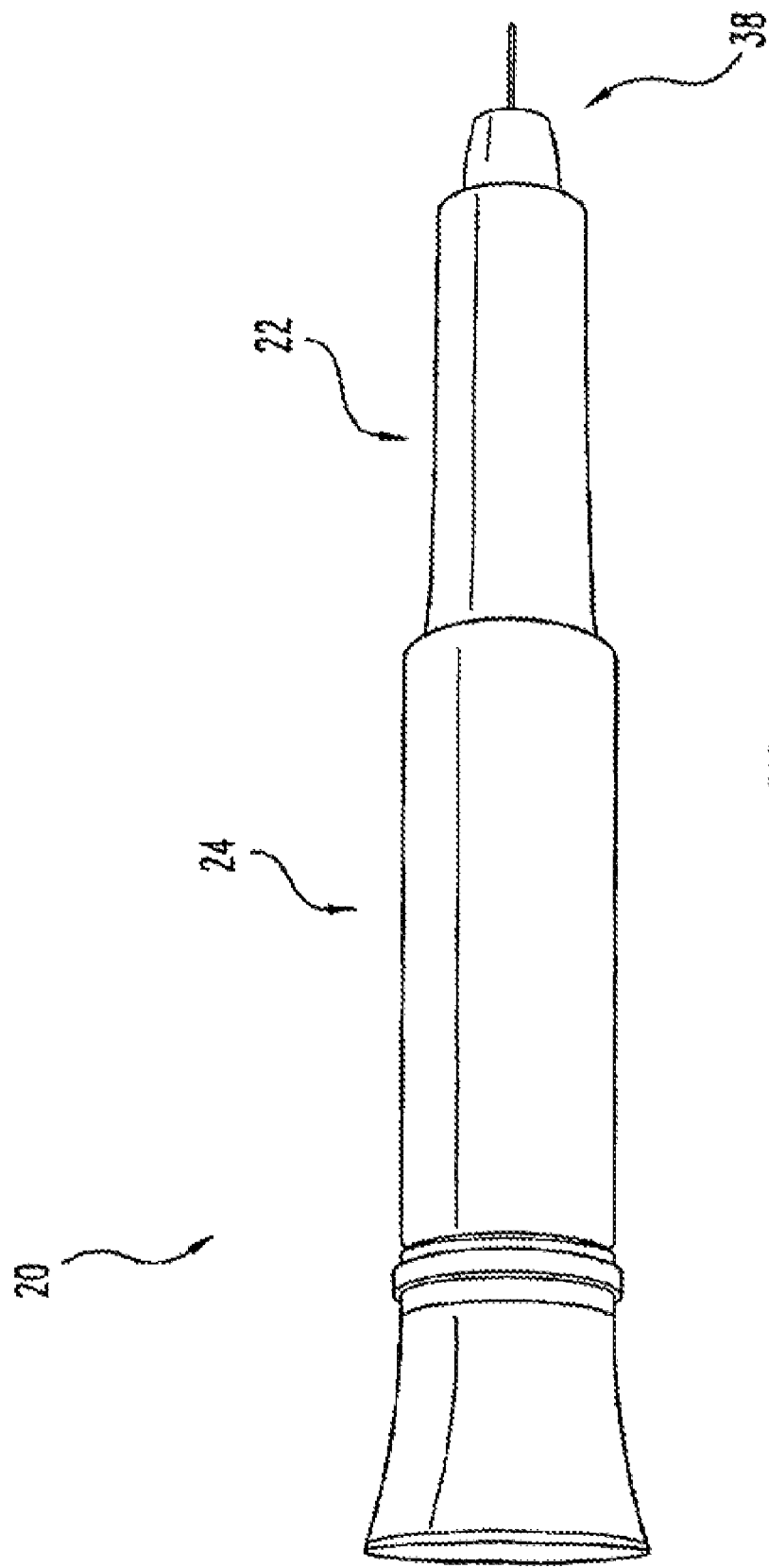
FIG. 1 is a diagrammatic perspective view of a first embodiment of a medication dispensing apparatus with pull/push to inject and rotate to prime mechanisms of the present invention.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
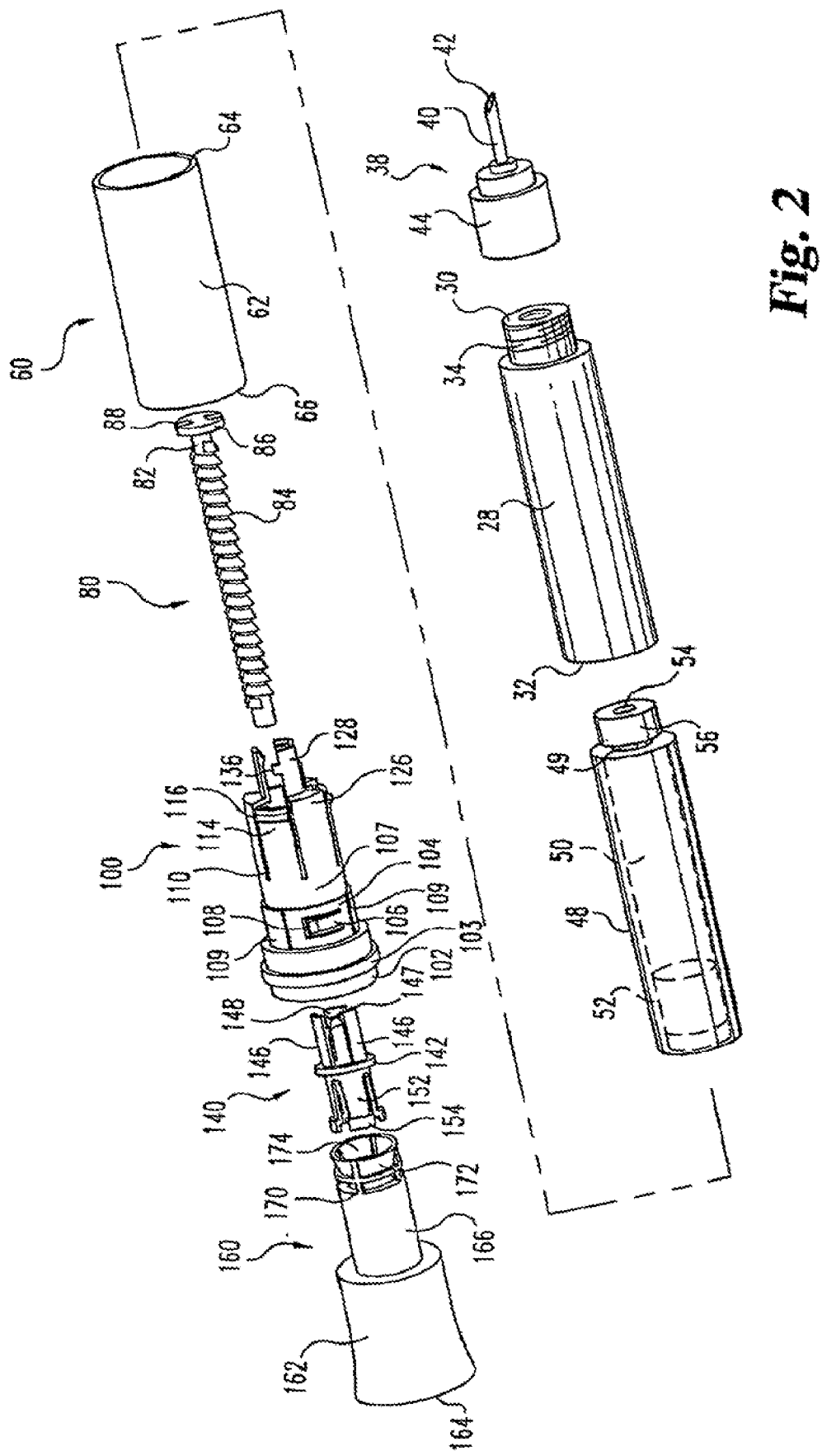
FIG. 2 is an exploded perspective view of the medication dispensing apparatus of FIG. 1.
Figure 3:
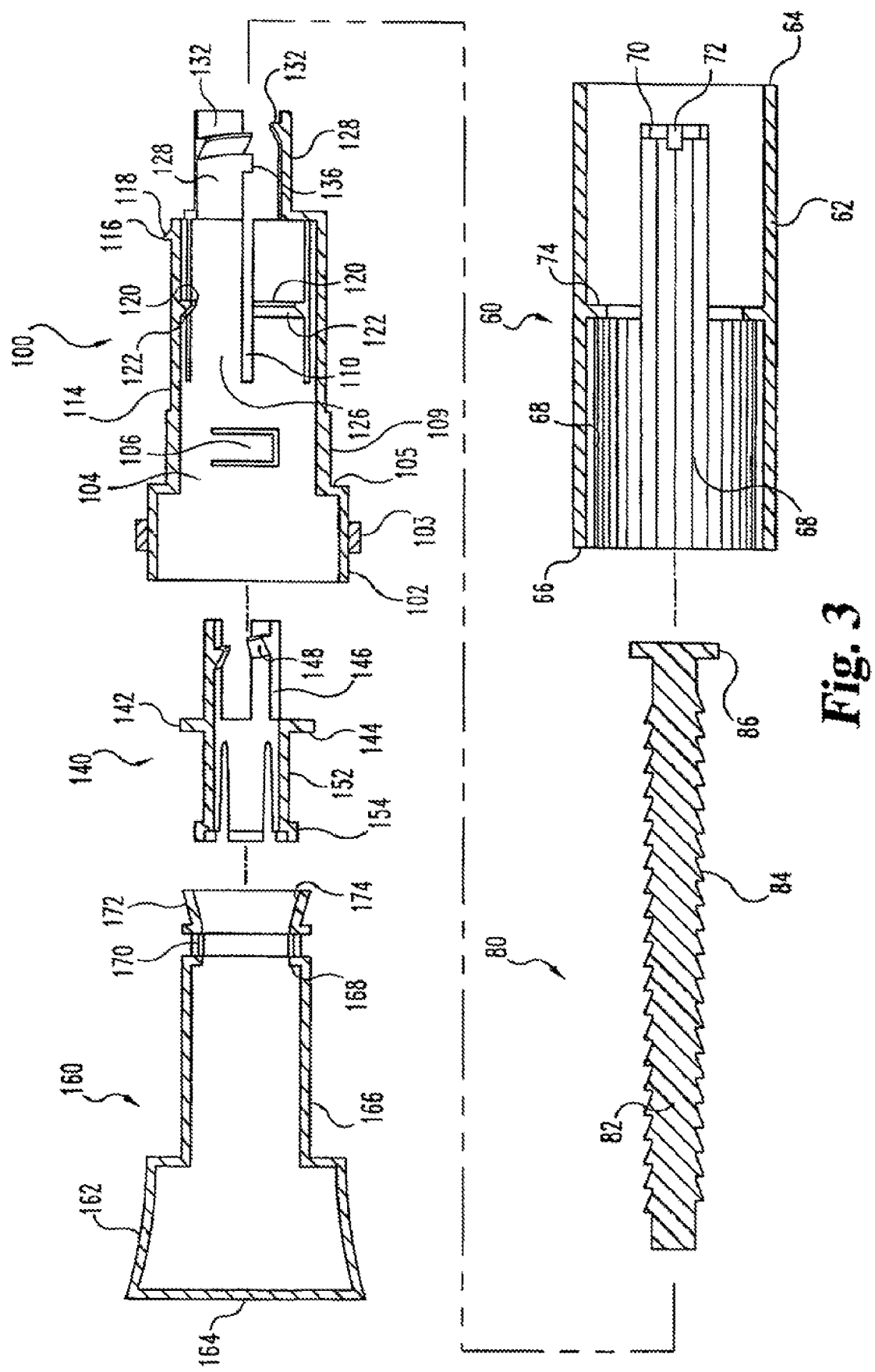
FIG. 3 is an exploded cross-sectional view of portions of the medication dispensing apparatus of FIG. 2.

Referring now to FIGS. 1 and 2, there is shown a first embodiment of a medication dispensing apparatus with rotate to prime and pull/push to inject functionality of the present invention. The apparatus, generally designated 20, is shown in a form commonly known as an injector pen, although other forms are within the scope of the invention. Medication injector pen 20 is a disposable pen, in that after the quantity of medicine contained therein is exhausted by multiple operations of the pen, the entire pen is discarded rather than being reset and reloaded with a replacement container of medicine. Pen 20 is repeatably operable to deliver into a user a fixed dose, i.e., a dose in an amount which is not settable by a user but which instead is in a specific amount dictated by the pen manufacturer by virtue of the particular design of the pen. While different injector pens, which are conceptually similar but slightly different in design, may be provided to allow for different fixed doses, each of such different pens is only adapted to repeatedly deliver a particular fixed dose.

Injector pen 20 includes a distal portion 22 with a distal needled end and which contains the medicinal fluid to be delivered upon pen operation, and a proximal portion 24 which contains the injecting and priming mechanisms used to force the contained medicine from the needled end. In the shown embodiment, distal portion 22 includes a retainer 28 and a cartridge 48 held therein. Cartridge retainer 28 is made of transparent plastic and includes a distal end 30 and a proximal end 32. External threading 34 around retainer distal end 30, or other suitable connection means, are used to releasably connect a pen-needle assembly generally designated 38.

Pen-needle assembly 38 is of known design and includes a double-ended needle cannula or injection needle 40 having a distal tip 42 at one end and a not-shown proximal point at the other. Injection needle 40 is mounted in a tubular hub 44 that is internally threaded to cooperate with the shown retainer design so as to be screwable onto and off of threading 34 of retainer distal end 30. Although the needle assembly is shown as having a single injection needle, needle assemblies which may be used with the present invention may be of various types known in the art, including, but not limited to, assemblies with one or more shortened injection needles, including microneedle arrays.

The proximal end 32 of cartridge retainer 28 includes an opening that receives a glass cartridge 48, and after receiving the cartridge the retainer proximal end 32 is fixedly mounted or secured, via adhesives, ultrasonic welding or in another suitable manner, to a previously subassembled pen proximal portion 24 when injector pen 20 is assembled by the manufacture.

Cartridge 48 is of conventional design and defines medicine-filled reservoir 50 which is closed at its proximal end by a piston 52 that is axially slidably and sealably engaged with the cartridge interior wall to hold the fluid medication within reservoir 50. The distal, outlet end of cartridge reservoir 50 is sealed by a septum 54 held by a cap 56 that is secured to a stepped-down diameter neck portion 49 of the cartridge. When pen-needle assembly 38 is mounted on the distal end of cartridge retainer 28 holding cartridge 48, the proximal point of injection needle 40 penetrates cartridge septum 54 to provide a fluid flow outlet by which medicine within cartridge reservoir 50 can be dispensed from needle tip 42 during operations of injector pen 20.

The fluid medicine container shown and described above is illustrative and not intended to be limiting as other constructions may be employed within the scope of the invention. For example, rather than having a distinct cartridge held within a separate retainer as in the shown fluid container, a fluid container may be provided in the form of an extension of the exterior housing of the pen into which are integrated the cartridge features. In another fluid container embodiment of the invention, the cartridge could be constructed to be sufficiently durable and adapted to secure directly to pen proximal portion 24 without any protective retainer therearound, and with the pen-needle assembly directly mountable to the cartridge.

With additional reference to FIGS. 3-8, pen proximal portion 24 of injector pen 20 consists of an external, protective housing 60, an axially advanceable drive member 80, a rotatable driver 100, a follower 140 and a plunger 160.

Housing 60 is injection molded as a single piece from a plastic material such as polycarbonate, and has a cylindrical, tubular body 62 with a distal end 64 and a proximal end 66. Distal end 64 is rigidly secured with cartridge retainer 28 when injector pen 20 is assembled by the manufacturer. Adjacent proximal end 66, the interior surface of body 62 includes a series of axially-aligned ratchet teeth 68 which continue uninterrupted around the entire internal circumference of the proximal end of the housing body. As best shown in the cross-sectional view of FIG. 7, ratchet teeth 68 have a one-way ramping so as to be engaged by the one or more pawls 108 used to prevent rotation in one particular direction relative to housing 60 of the pawl-mounting driver 100. Although ratchet teeth 68 number thirty-six in the shown embodiment, fewer or additional teeth which provide suitable anti-rotation capabilities may be used.

Figure 8:
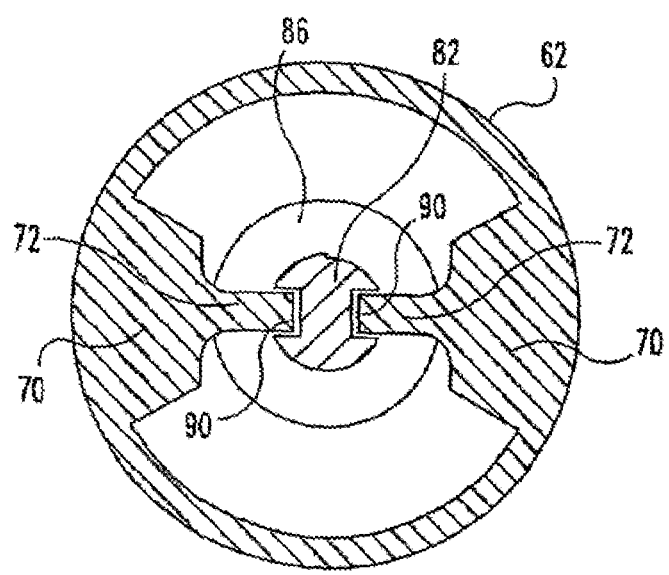
FIG. 8 is a cross-sectional view taken along line 8-8 of FIG. 6.
Figure 9:
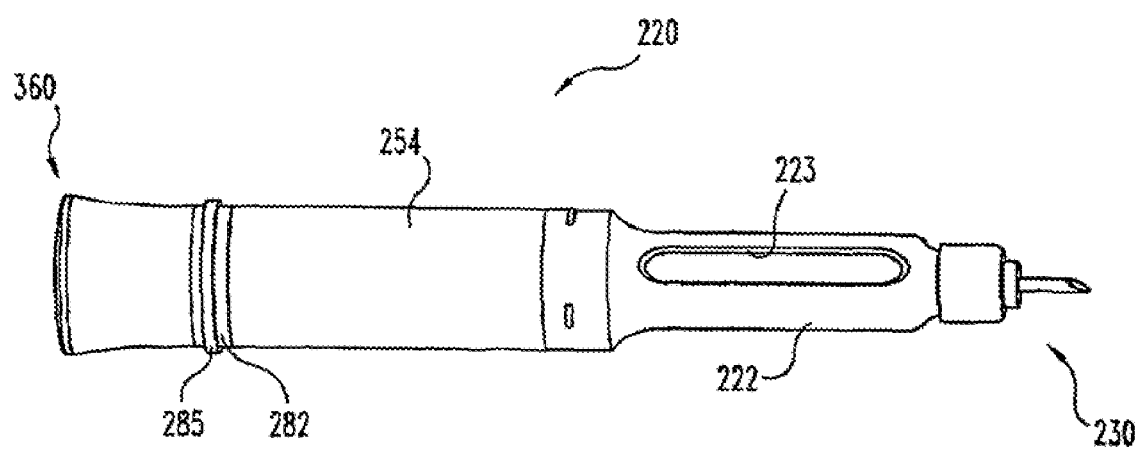
FIG. 9 is a diagrammatic perspective view of another embodiment of a medication dispensing apparatus with pull/push to inject and rotate to prime mechanisms of the present invention.
Figure 10:
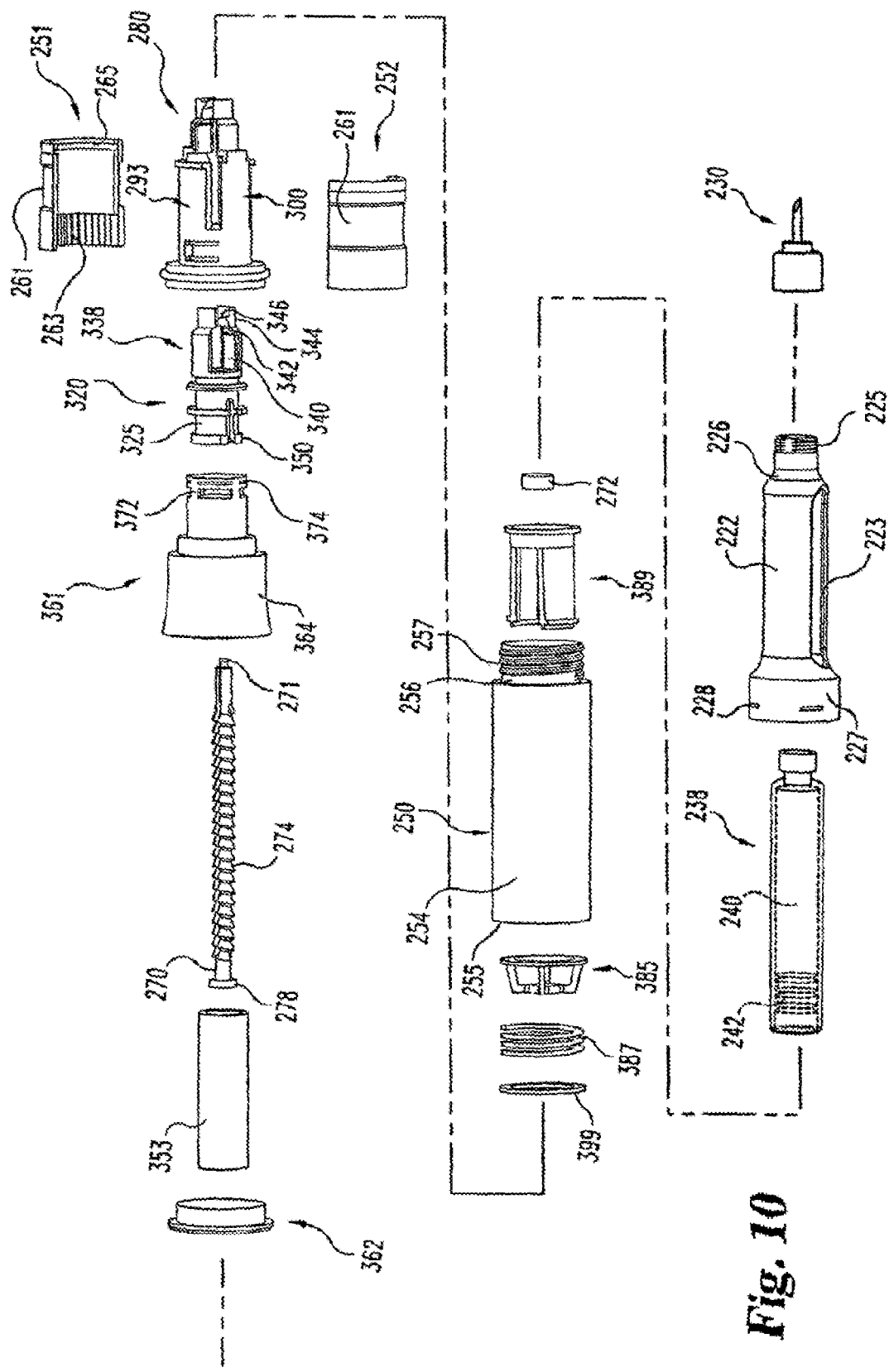
FIG. 10 is an exploded perspective view of the medication dispensing apparatus of FIG. 9.
Figure 11:
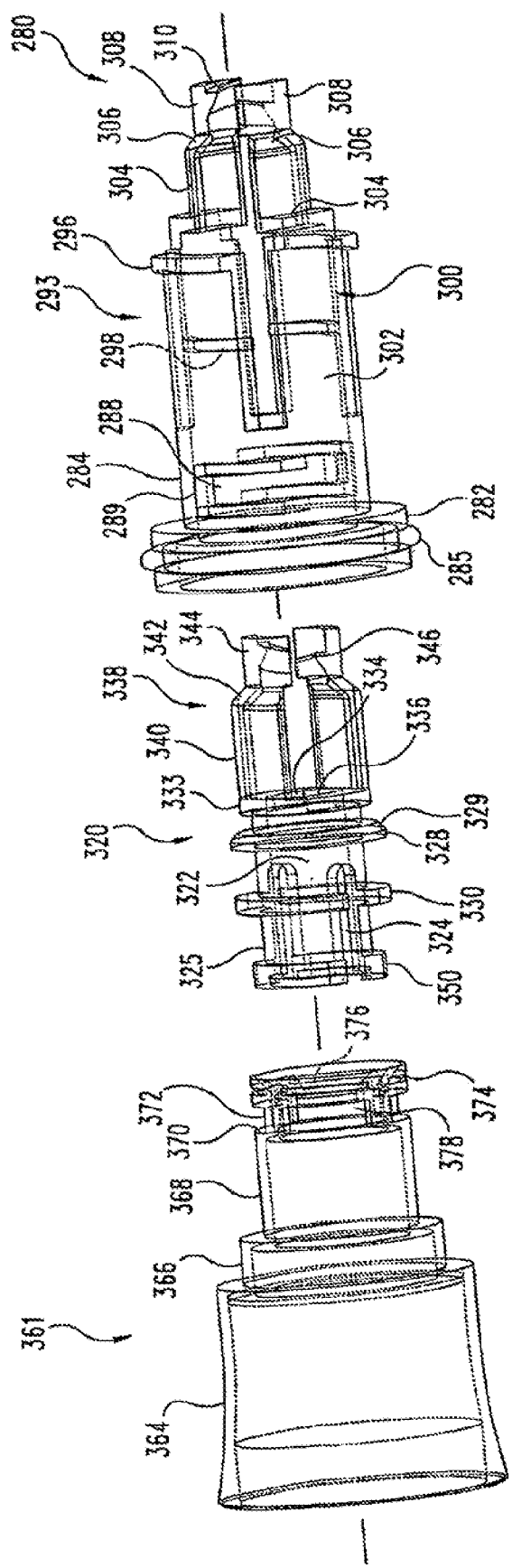
FIG. 11 is an exploded perspective view of portions of the apparatus FIG. 10.
Figure 12:
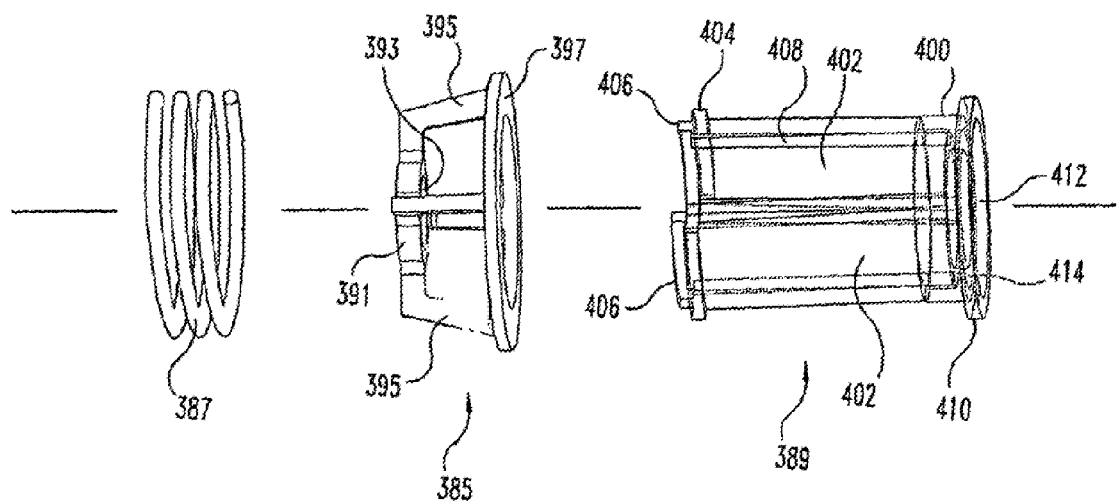
FIG. 12 is an exploded perspective view of other portions of the apparatus of FIG. 10.

Near distal end 64, housing body 62 includes at least one, and preferably a pair of tabs 70, used to engage drive member 80 to prevent its rotation relative to housing 60. As best shown in FIG. 8, tabs 70 project radially inward from diametrically opposed regions of the housing body interior surface, and include rectangular-shaped heads 72. Heads 72 jut proximally from tabs 70, and further extend to body 62 to serve as reinforcing ribs for tabs 70. Tab heads 72 fit within grooves 90 of drive member 80.

On the body interior surface at an axial position between anti-rotation tabs 70 and proximal end 66 is a circumferentially extending shoulder 74 that juts radially inward approximately twice the distance as the peaks of ratchet teeth 68. Shoulder 74 serves as a latching point for driver 100. Shoulder 74 is continuous around the housing body internal circumference except for two sections where ratchet teeth 68 extend through toward anti-rotation tabs 70. These two sections are provided to facilitate a one-piece molding of the shown body, and in embodiments where the shown housing is formed from multiple pieces, such as mating halves assembled together, these interruptions of shoulder 74 may be eliminated.

Drive member 80 is in the form of a drive screw that is injected molded from plastic such as polycarbonate as a single-piece. Drive screw 80 has a shaft 82 with external threading 84 along essentially its entire axial length. Threading 84 is a single thread that is generally right triangular in axial cross-section, with a flat edge aligned perpendicular to the axial direction and facing the proximal direction, and which spirals along the shaft 82 to create a helical pattern. A multiple start thread alternatively may be used to create a suitable threading.

The distal end of drive screw 80 includes a foot 86 that has a larger surface area than the transverse cross-sectional area of shaft 82 to distribute loading on the cartridge piston 52 that foot 86 contacts and thereby directly engages during piston advancing. Two rectangular notches 88 in the periphery of foot 86 are aligned with a pair of diametrically arranged and longitudinal grooves 90 formed in screw 80. Grooves 90, which have a squared-off shape and a smooth base, extend the entire axial length of shaft 82 and slidably accommodate anti-rotation tab heads 72 which permit translation of drive screw 80 relative to housing 60. Foot notches 88 allow introduction of tab heads 72 into grooves 90 during assembly by the manufacturer of the one-piece housing 60 to the subassembly shown in FIG. 4, which shown subassembly results from screw 80 being screwed during assembly into a subassembly consisting of follower 140, plunger 160, and driver 100. While the number of grooves 90 preferably corresponds to the number of anti-rotation tab heads 72 which may be fewer or greater in number, the number of such grooves and tabs is preferably limited to two as shown so as to ensure a durable, rotation preventing construction while creating only limited interruptions to the threading.

Priming driver 100 is injection molded from a resilient plastic material such as ABS. Driver 100 includes a tubular, cylindrical grip portion 102 that at its distal end is stepped down to a tubular, cylindrical body portion 104, which is further stepped down to body portion 107. Grip portion 102 has an outer diameter that generally conforms to the outer diameter of housing body 62 so as to blend into the housing proximal end 66 to which it is adjacent. Grip portion 102 is the part of driver 100 which is externally accessible to be manually rotated by a user for pen priming purposes. To facilitate being turned by contact with one or more of a user's fingers during pen priming, grip portion 102 preferably is provided with an elastomeric ring 103 having a high coefficient of friction and which is fixedly secured, such as via friction fit or possibly with adhesives, around the outer radial periphery of the grip portion. Rather than the shown ring 103, grip enhancing features, such as radial protrusions integrally formed thereon, may be molded into grip portion 102, in which case driver 100 may be entirely formed of a one-piece molded construction.

Figure 7:
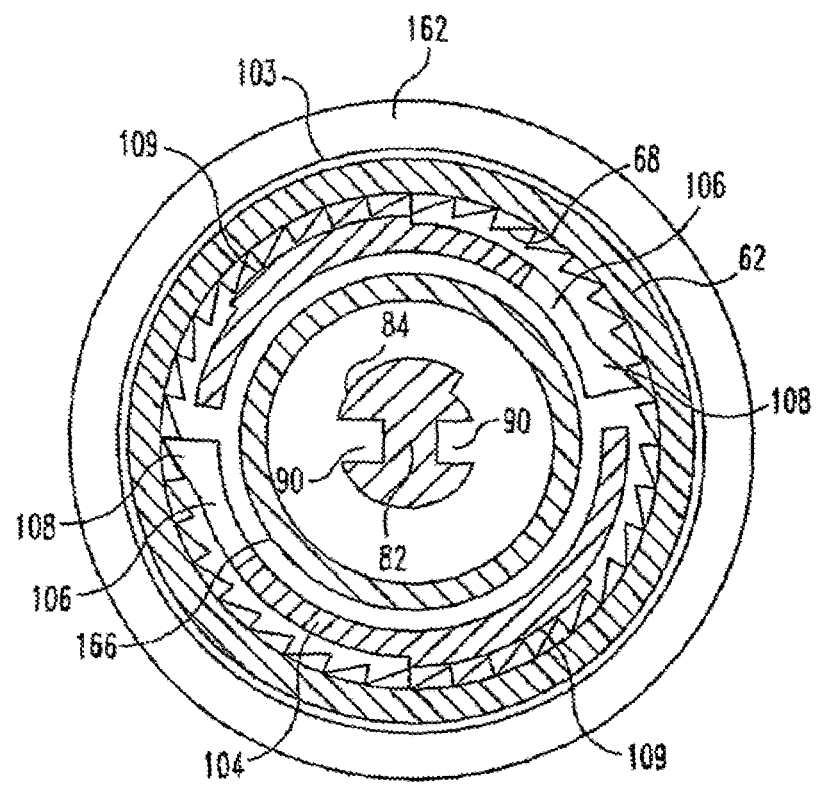
FIG. 7 is a cross-sectional view taken along line 7-7 of FIG. 5.

Driver body portion 104 extends distally from grip portion 102 and is sized to insert within the interior hollow of housing body 62. Within a proximal region of body portion 104, at least one pawl is formed which cooperates with ratchet teeth 68 to limit the rotation of driver 100 relative to housing 60 to a single direction. In the shown driver 100, a pair of nearly diametrically opposed pawls are provided in the form of angularly extending, radially bendable pawl fingers 106 having catch ends 108 that extend sufficiently far radially outward to engage ratchet teeth 68. By slightly offsetting the pawls so as to not be precisely-diametrically opposed, as shown in FIG. 7, one catch end 108 can engage a ratchet tooth 68 while the other catch end 108 is being ramped inward by contact with the middle of a different ratchet tooth 68, whereby the angular precision of the offset pawls is twice as good as if lined up diametrically. From the perspective of a FIG. 7 viewer, priming driver 100 can be rotated in a counterclockwise direction relative to housing 60 as pawl fingers 106 are forced to bend radially inward, and then snap radially outward, as catch ends 108 slide along the ramped surfaces of ratchet teeth 68, and then drop over the teeth peaks. Priming driver 100 is prevented from being rotated in a clockwise direction relative to housing 60 by the engagement of one of the pawl catch ends 108 with the radially-aligned stop face of a ratchet tooth 68. This restriction on rotation not only ensures that a user will revolve priming driver 100 in the proper direction to achieve pen priming, but also, due to the connection of the driver with the drive screw described further below, prevents the drive screw from hacking up or moving proximally which may result in an incorrect dose.

Body region 107 further includes a pair of raised portions 109. Raised portions 109 are diametrically opposed and are in closer proximity to ratchet ribs 68 than body region 107 so as to stabilize driver 100 within housing 60.

The distal region of driver body portion 107 is divided by a plurality of slot-shaped notches 110 into two sets of axially extending, radially resilient fingers. The first set of fingers, generally designated 114, are used to assemble driver 100 to housing 60 and follower 140 to driver 100, and are identically shaped. Fingers 114 are three in number in injector pen 20 and are centered 120° apart. Each finger 114 includes a latching rib 116 and a stop rib 120. Each latching rib 116 projects radially outwardly from an outer surface of its respective finger 114 near the disc end thereof. Each stop rib 120 projects radially inwardly from an inner surface of its respective finger 114 at an axial location proximal of rib 116. The distal face of each rib 116 has a ramped or camming surface 118, and the proximal face of each rib 120 has a camming surface 122.

Figure 4:
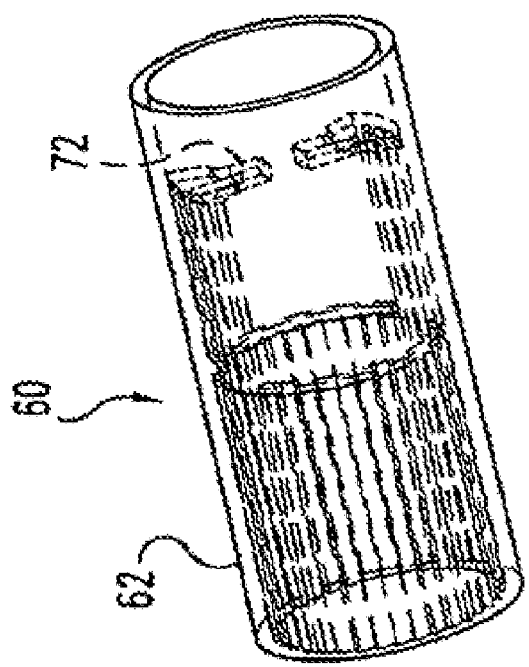
FIG. 4 is a perspective view of portions of the medication dispensing apparatus of FIG. 1 during assembly.
Figure 4:
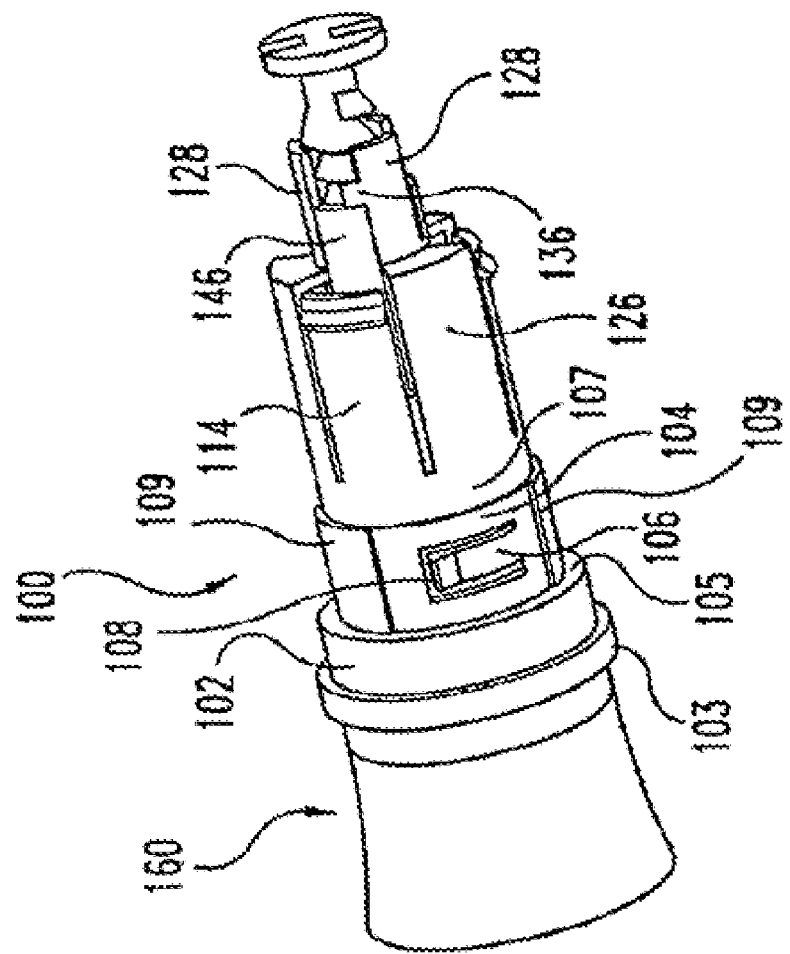

Latching ribs 116 cooperate with the distal face of housing shoulder 74 to axially retain driver 100 within housing 60. During manufacturing assembly, as the subassembly including driver 100 is inserted distally into housing 60 as shown in FIG. 4, the engagement of all of the camming surfaces 118 with shoulder 74 bends the distal ends of fingers 114 inwardly so as to allow ribs 116 to pass over shoulder 74, at which time fingers 114 snap outward due to their resilient construction, thereby latching ribs 116 to shoulder 74 to prevent proximal withdrawal of driver 100. Ribs 116 are axially positioned such that when snapped into latching engagement with shoulder 74, the housing proximal end 66 is in closely spaced relationship with annular shoulder 105 of grip portion 102, and further axial insertion in a distal direction of driver 100 within housing 60 is prevented by the abutment of shoulder 105 with the end of the housing.

The second set of fingers, generally designated 126, include L-shaped extension portions 128 and are used to engage drive screw 80 to convert driver rotation into drive screw axial motion. The base of each of the three fingers 126 proximal of extension portions 128 is located between successive fingers 114, and fingers 126 are centered 120° apart. A stop tab 136 laterally projects from a central region of each of finger extension portions 128.

A projecting thread segment 132 is formed on a radial inner surface of each extension portion 128 and mates with external threading 84 of drive screw 80. To completely mate with threading 84, each thread segment 132 is positioned at a different axial position on its respective extension portion 128 such that the thread segments 132, but for the interruptions resulting from the circumferential or angular spacing of extension portions 128, form part of a continuous helical thread with the same pitch as threading 84 of screw 80. As further shown in FIG. 5 and 6, each thread segment 132 in axial cross-section has a ramped proximal face 133 and a radially-aligned stop face 134. The resilient construction of driver 100 allows extension portions 128 to splay outward such that thread segments 132 can axially slide over screw threading 84 when the drive screw is advanced during injecting as described below. In particular, thread segments 132 slide along the ramped thread face and then insert within the indentation formed by the radial drop off between the axial end of one pass of threading 84 and the start of the adjacent pass of the threading.

While three of each of fingers 114 and 126 are shown, fewer or additional fingers may be used within the scope of the invention. For example, as few as one finger with extension portion 128 may be provided, although at least two are used to achieve a secure, direct engagement with the drive screw threading 84. In addition, as fingers 114, and thereby the base of fingers 126, result from notches 110 that provide flexibility for snap insertion of the driver into a one-piece housing, and the follower into the driver, if a multiple piece housing which can be assembled around the priming driver is used, and the follower were adapted to flex inward during assembly, fingers 114 and the base of fingers 126 could be eliminated, and their features incorporated into a continuous sleeve.

Axially movable within the internal hollow of driver 100 is a follower, generally designated 140, which is injection molded as a single piece from a resilient plastic material such as acetal. Follower 140 includes a central annulus 142 with a proximal surface 144 that abuts stop ribs 120 during pen cocking as described below. During manufacturing assembly, as follower 140 is inserted distally into driver 100, annulus 142 engages camming surfaces 122 to bend fingers 114 outwardly so as to allow annulus 142 to pass over ribs 120, at which point fingers 114 resiliently snap back inward to prevent proximal withdrawal of follower 140.

At least one finger, and preferably two or more, such as the three fingers 146 shown in injector pen 20, extend distally from the inner radial region of annulus 142 to engage drive screw 80. The three fingers 146 are generally rectangular in shape and centered 120° apart. Each finger 146 includes a distal end 147, and an inwardly projecting thread segment 148 formed on a radial inner surface. In the preferred embodiment, each thread segment 148 mates with external threading 84 of drive screw 80, and to fit properly therewith each thread segment 148 is positioned at a different axial position on its respective finger 146 to be aligned as separated pieces of a continuous helical thread. As further shown in FIGS. 5 and 6, each thread segment 148 in axial cross-section has a ramped proximal face 149 and a radially-aligned drive face 150. The resilient construction of follower 140 allows fingers 146 to splay outward as the follower is pulled proximally by plunger 160 during pen cocking as described below, such that thread segments 148 can axially slide over the threading 84 of rotatably fixed screw 80.

In injector pen 20, follower 140 uses its engagement with the screw threading to force drive screw 80 axially during injecting as described below. To maintain helical thread alignment between the follower and screw and the driver and screw, the follower 140 is keyed to driver 100 to rotate therewith. This keying is achieved by each follower finger 146 closely fitting within the space between adjacent driver finger extension portions 128. Driver 100 and follower 140 may be suitable keyed together in alternate manners in different embodiments, such as via a spline that fits within an added notch in annulus 142, or a pin and slot.

In another embodiment which is not shown, a follower does not act against the drive screw threading during injecting, but rather against at least one rack of axially spaced teeth distinct from threading 84 and which extends longitudinally along the drive screw. In this design, the follower does not rotate with driver 100, but rather is rotationally fixed to the drive screw. One suitable rack for this alternate design uses a pair of racks, one formed within each groove 90, and the resilient follower fingers are two diametrically opposed fingers that include transversely extending teeth rather than the projecting thread segments 148 so as to mesh with the racks.

A plurality of mounting fingers 152, such as the four shown, extend proximally from the inner radial region of annulus 142. Latches 154 jut radially outwardly from the proximal ends of fingers 152.

Plunger 160 is injection molded from a lightweight material such as polycarbonate. Although shown as having a one-piece construction, to facilitate manufacture plunger 160 is formed of multiple parts assembled together, such as a tubular main body with a cap over the proximal end of the main body. Plunger 160 includes a grip portion 162 extending distally of driver 100 which is externally accessible to be manually pulled by a user for pen cocking purposes. Along its length in the proximal direction, grip portion 162 is radially outwardly flared so as to be more readily grasped by user, such as between the thumb and fingers of a user, when pulled to the left from the perspective of a viewer of FIG. 1, Other graspable grip portion configurations may be substituted, such as a loop in which a finger can insert, or a bar under which fingers can be looped. The proximal end 164 of plunger 160 serves as a push surface against which a force can be applied to push the plunger of a cocked pen to the right from the perspective of a viewer of FIG. 1.

The distal end of grip portion 162 is stepped down to a cylindrical tube portion 166 that fits within the interior hollow of driver 100 and is slidable into and out from such hollow during use of pen 20. An inward lip 168 is formed at the distal end of tube portion 166, and four circumferentially spaced bars 170 axially project from the lip and support a plunger ring portion 172 including a frustroconical inner surface 174. The space between ring portion 172 and lip 168 defines a recess or groove 176 around the inner circumference of plunger 160 and inward of bars 170 which in injector pen 20 is used to connect plunger 160 with follower 140 so as to be axially fixed but rotatably free or free wheeling.

During manufacturing assembly, as follower 140 is inserted proximally into plunger 160, the engagement of latches 154 by inner surface 174 bends the proximal ends of mounting fingers 152 inwardly until latches 154 pass inner surface 174, at which time fingers 152 snap outward due to their resilient construction, thereby inserting latches 154 within groove 176 and latching the proximal face of ring portion 172 to prevent distal withdrawal of follower 140 as plunger 160 is moved proximally. The proximal face of latches 154 abuts inward lip 168 to prevent over insertion of follower 140, and to cause axial motion of plunger member 160 in a distal direction to axially move follower 140 distally. Latches 154 are slidable within groove 176 such that rotation of follower 140 does not necessarily cause rotation of plunger 160, and vice versa.

Figure 5:
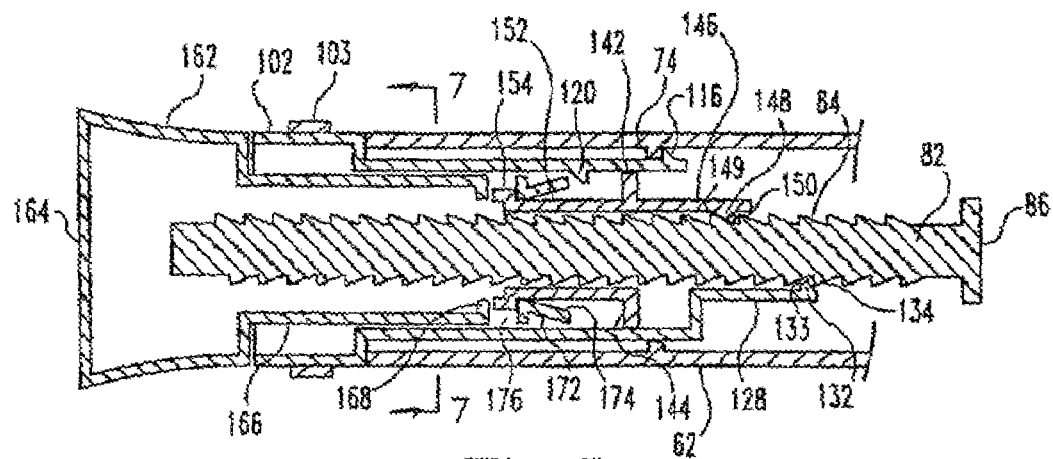
FIG. 5 is a diagrammatic cross-sectional view of the proximal parts of the medication dispensing apparatus of FIG. 1 in a ready or ready-to-be-cocked state.
Figure 6:
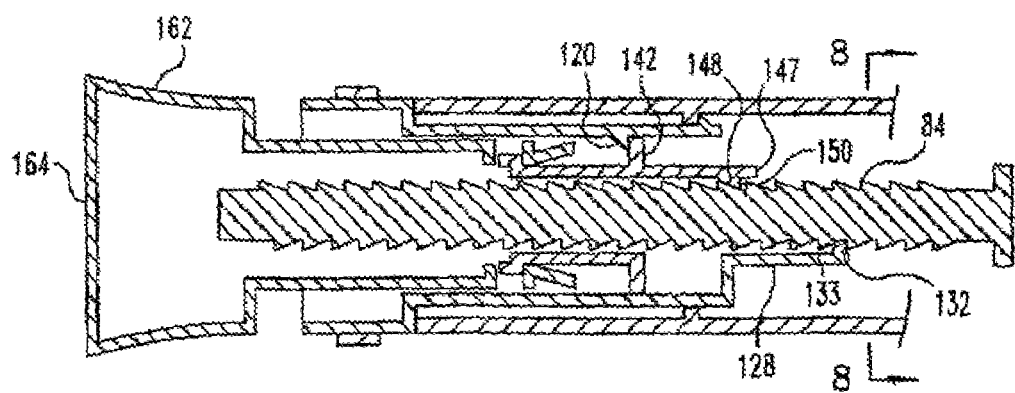
FIG. 6 is a cross-sectional view conceptually similar to the view of FIG. 5, but after the apparatus has been manipulated from its ready-to-be-cocked state to a cocked or ready-to-inject state.

The structure of injector pen 20 will be further understood in view of the following explanation of its operation given with primary reference to FIGS. 5 and 6. Initially, a user requiring a dose of medication will locate pen 20, which normally will be in the ready arrangement shown in FIG. 5, which is the arrangement in which the pen remained after its previous use, or in which the pen is provided to a user for its first use.

Pen 20 is first primed. Typically while clutching the housing 60 and/or distal portion 22 in one hand while pointing the needle tip 42 upward, a user grips driver grip portion 102 using one or more digits of her other hand, with slippage limited by ring 103, and begins to manually rotate it and thereby all of the rest of priming driver 100 relative to housing 60. Driver 100 can only be rotated within the housing in one direction, as the engagement of the pawl teeth 108 with ratchet teeth 68 prevent rotation in the opposite direction. The rotation of finger extension portions 128 during driver rotation causes drive screw 80, due to it being rotationally fixed relative to the housing 60 by tab beads 72, to axially translate in the distal direction, or to the right in FIG. 5. In particular, because thread segments 132 engage threading 84 of drive screw 80, as thread segments 132 are rotated, due to the screw being rotatably fixed and driver 100 being prevented from axially moving within the housing in the proximal direction by the latching of ribs 116 with housing shoulder 74, screw 80 is forced to translate distally. As drive screw 80 translates distally, the cartridge piston 52 which is not shown in FIGS. 5 and 6 is pushed distally by foot 86, thereby deceasing the reservoir volume for the medication in the cartridge such that medication is forced toward needle tip 42. Normally, foot 86 will be in contact with piston 52 at the start of the priming, but rotation of the priming driver, before causing piston 52 to move, will naturally close up any gap between foot 86 and piston 52, such as most likely to exist during the first ever use of pen 20. Driver 100 is able to be continuously rotated by a user during priming, whether it be through a fraction of a revolution, or one or more revolutions, until the user sees that the piston movement has caused medicine to reach the upward pointed needle tip 42 as all air is expelled, at which time the user stops twisting driver 100 as priming is complete.

During pen priming, follower 140 rotates with driver 100 due to its keying together, but because of the free wheeling connection of plunger 160 with follower 140, plunger 160 does not have to rotate as well, and therefore any restriction on twisting of the plunger does not hinder priming.

After priming, pen 20 is ready to be used for injection. A pulling stop is first performed to cock or prepare the uncocked pen 20 to deliver the dose for which it has been designed. During that pulling step, and again while housing 60 and/or distal portion 22 is grasped in one hand, a user uses her other hand to pull plunger grip portion 162 axially away from driver 100 and housing 60. Plunger grip portion 162 is pulled proximally a fixed distance, specifically until shoulder 144 of follower 140, which is also being pulled rearward due to its connection with the plunger, abuts stop ribs 120, which abutment halts the axial movement of plunger 160. During this follower movement, the distal ends of fingers 146 first flex or bend radially outward as the ramped proximal faces 149 of thread segments 148 slide up the ramped distal face of the threading 84, and then snap back inward as thread segments 148 slip over the peaks of the thread. In injector pen 20, the distance the follower axially moves is only slightly greater than the pitch of threading 84, such that each thread segment 148 only slides over threading 84 once during a pen cocking, which threading, along an axial cross-section of the drive screw serves as a series of axially spaced projections for engagement with the finger thread segments. In alternate embodiments, follower 140 can be adapted to slide past multiple thread passes or projections during its retraction. As follower thread segments 148 slip over threading 84, drive screw 80 is prevented from being pulled proximally by the abutment of threading 84 with stop faces 134 of the driver thread segments 132. In addition to the tactile signal resulting from the follower annulus 142 bumping against driver rib 120, the completion of the withdrawal stroke of plunger 160 may be indicated in other ways, such as is disclosed in U.S. Patent Application Ser. No. 60/279070 entitled "MEDICA- TION DISPENSING APPARATUS CONFIGURED FOR PULL TO SET DOSE AND PUSH TO INJECT SET DOSE FUNCTIONALITY," the entire disclosure of which is incorporated herein by reference.

At this point in time, pen 20 has been cocked or prepared to deliver the medicine dose it was designed to inject, and is arranged in the ready-to-inject state shown in FIG. 6. If a user has not previously primed pen 20, or has forgotten that priming has been performed, due to the fact that driver thread segments 132 always engage drive screw threading 84, driver grip portion 102 can still be twisted to cause priming of the pen without moving the pen from its cocked state. Advantageously, such priming does not alter the volume of medicine to be delivered by subsequent plunging of the cocked plunger 160.

To actually inject the medicine, after pen 20 is manipulated so the injection needle distal tip 42 properly penetrates a user's skin, or other injection site, an axial, distal plunging force is applied to push surface 164 to force plunger 160 distally. As follower 140 is moved distally by plunger 160, the abutment of drive screw threading 84 by drive faces 150 of thread segments 148 causes drive screw 80 to translate distally to shift piston 52 and force medication through needle 40. In particular, the pitch of screw threading 84 is selected such that the force necessary to advance piston 52 within cartridge 48 is less than the input force that would be required to overcome the force of friction between thread segments 148 and threading 84, and therefore screw 80 is advanced instead of follower 140 being rotated. During this drive screw advancement, the distal ends of finger extension portions 128 flex or bend radially outward as the ramped faces 133 of thread segments 132 slide up the ramped distal face of the passing thread 84, and then snap back inward as the peaks of the threading pass thread segments 132. Plunging motion of plunger 160, and thereby advancement of drive screw 80, is stopped, and the medicine injection is complete, when the distal ends 147 of all the follower fingers 146 simultaneously abut stop tabs 136 of finger extension portions 128.

Pen 20 can continue to be used to deliver its fixed dose until the medicine remaining in the cartridge is insufficient for a proper dosing, which insufficiency may be indicated to a user by her inability to fully withdraw the plunger to cock the apparatus due to, for example, the follower engaging a not shown stop associated with the drive screw. When insufficient medicine remains, pen 20 is to be disposed of and replaced with a similar but entirely new pen.

Referring now to FIGS. 9-15, there is shown another embodiment of a medication dispensing apparatus with rotate to prime and pull/push to inject functionality of the present invention. The apparatus, generally designated 220, serves as a reusable injector pen, in that after the quantity of medicine contained in a cartridge therein is exhausted by multiple operations of the pen, the cartridge can be removed and replaced with a full cartridge, and the pen otherwise reset, to be used again. As with injector pen 20, pen 220 is operable to deliver into a user a particular fixed dose per each use. As will be recognized by the skilled artisan, the designs of injector pen 220 and pen 20 are in many respects similar, and therefore not only are similar parts of injector pen 220 not all exhaustively detailed below, but also certain parts of injector pen 20 could be correspondingly modified.

The distal portion of injector pen 220 includes a one-piece retainer 222 and a medication cartridge 238 held therein. Cartridge 238 is identical to cartridge 48 and includes a medicine-filled reservoir 240 and a slidable piston 242. Cartridge retainer 222 is made of an opaque plastic but includes two windows 223 through which the cartridge contents are visible. External threading 225 around the retainer distal end 226 is used to releasably connect a pen-needle assembly 230, identical to pen-needle assembly 38, such that the proximal point of the injection needle of assembly 230 penetrates the cartridge septum to provide a fluid flow outlet by which medicine within cartridge reservoir 240 can be dispensed during injector pen use.

A collar portion 227 at the proximal end of cartridge retainer 222 includes a central opening through which a cartridge 238 is loaded and unloaded. A series of detents 228 on the exterior surface of collar portion 227 allow for the snap fit attachment of a not shown pen cap via a mating indent or groove in that cap. Collar portion 227 includes a means for removably mounting retainer 222 to the housing of the proximal portion of injector pen 220. Such means are shown as an internal threading 229 that connects to an external threading 257 of housing outer shell 250. Other suitable forms of removably mounting the retainer, such as via a bayonet type connection or other connection systems known in the art, may be substituted within the scope of the invention.

The form of removably mountable fluid medicine container shown in the embodiment of FIGS. 9-15, which uses a disposable cartridge and a reusable retainer, is merely illustrative and not limiting. Other forms of fluid containers, including but not limited to a fluid container comprising a disposable retainer and a disposable cartridge, which retainer is fixedly attached to the cartridge so as to be disposed of together, and where that fluid container is replaced as a combination fresh cartridge/retainer, may be employed within the scope of the invention.

The proximal portion of injector pen 220 includes a multi-part housing formed of the outer shell 250, and a pair of inner shell halves 251 and 252, each made from a plastic material such as polycarbonate. Shell halves 251 and 252 are identical in injector pen 220, and therefore further description of shell half 251 has equal application to shell half 252. Shell halves 251 and 252 need not be identical to function properly.

The multi-part housing construction facilitates pen manufacture, as during manufacture inner shell halves 251 and 252 are secured together around the priming driver 280 described further below and fixedly secured within and to outer shell 250, for example with adhesive applied along glue groove 261 of the shell halves or with other suitable fasteners. This fixed securement results in shell halves 251, 252 being axially and rotatably fixed in outer shell 250. Shell halves 251 and 252 are designed to contact each other on both angular ends when secured together around the driver.

Outer shell 250 has a tubular body 254 with a proximal end 255 and a distal end portion 256 which is stepped down in diameter and externally threaded at 257 to removably mount cartridge retainer 222. Near distal end portion 256, the interior surface of housing body 254 includes a pair of diametrically opposed, radially inwardly projecting tabs 259 (see FIG. 14) used to engage the drive screw to prevent its rotation relative to housing 250.

The interior surfaces of shell halves 251 and 252 define a series of axially-aligned ratchet teeth 263. In a finally assembled injector pen 220, teeth 263 continue uninterrupted around the entire internal circumference of the pen housing. Ratchet teeth 263 have a one-way ramping so as to be engaged by the one or more pawls 288 used to prevent rotation in one particular direction of the pawl-mounting driver 280 relative to the pen housing.

The axially advanceable drive member in injector pen 220 is a drive screw that includes a drive screw shaft 270 and a screw head 272, each injected molded from plastic such as polycarbonate. Drive screw shaft 270 has external threading 274 along essentially its entire axial length. Threading 274 is a single thread that is generally right triangular in axial cross-section, with a flat edge aligned perpendicular to the axial direction and facing the proximal direction, and which spirals along the shaft 270 to create a helical pattern. A pair of diametrically arranged and longitudinal grooves 276 formed in shaft 270 have a squared-off shape and a smooth base, and extend essentially the entire axial length of shaft 270 to slidably accommodate anti-rotation tabs 259 that permit translation of the drive screw relative to the pen housing. Drive screw head 272 snap fits in a conventional manner onto a lipped nub 271 at the distal end of drive screw shaft 270. Screw head 272 distributes loading on the cartridge piston 242. The proximal end of drive screw shaft 270 includes a radially protruding head 278 that serves as an insufficient remaining dose stop as described further below.

The priming driver, generally designated 280, is injection molded from a resilient plastic material such as ABS. Driver 280 includes a tubular, cylindrical grip portion 282 that at its distal end is stepped down to a tubular, cylindrical body portion 284. Grip portion 282 has an outer diameter that generally conforms to the outer diameter of housing outer shell 250 so as to blend into the housing end 255 to which it is adjacent. An elastomeric or O-type ring 285 fits tightly so as to be non-rotatable within a circumferential groove in grip portion 282. O-ring 285 makes it easier for a user to grip the driver, and further improves the aesthetics. Grip portion 282 and its grip ring 285 is the part of driver 280 which is externally accessible to be manually rotated by a user for pen priming purposes.

Driver body portion 284 extends distally from grip portion 282 and is sized to insert within the interior hollow formed by inner shell halves 251 and 252. A pair of nearly diametrically opposed pawls are provided in the form of angularly extending, radially bendable pawl fingers 288 having catch ends 289 that extend sufficiently far radially outward to engage ratchet teeth 263 to limit the rotation of driver 280 relative to shell halves 251, 252 to a single direction. In particular, priming driver 280 can be rotated in a first direction relative to the pen housing as pawl fingers 288 are forced to bend radially inward, and then snap radially outward, as catch ends 289 slide along the ramped surfaces of ratchet teeth 263, and then drop over the teeth peaks. Priming driver 280 is prevented from being rotated in the direction opposite to the first direction relative to the pen housing of injector pen 220 by the engagement of one of the pawl catch ends 289 with the radially-aligned stop face of a ratchet tooth 263.

The distal region of driver body portion 284 is divided by a plurality of slot-shaped notches into two sets of axially extending, radially resilient fingers. The first set of fingers, generally designated 293, are identically shaped and used to assemble driver 280 to the pen housing, as well as follower 320 to driver 280. Fingers 293 are two in number and centered 180° apart. Each finger 293 includes a mounting rib 296 and a stop rib 298. Each mounting rib 296 projects radially outwardly from an outer surface of its respective finger 294 near the distal end thereof. Each stop rib 298 projects radially inwardly from an inner surface of its respective finger 294 at an axial location proximal of rib 296.

Mounting ribs 296 fit into and slide within groove 265 of shell halves 251, 252 arranged around the driver 280. When shell halves 251, 252 are secured within housing 250, the interfitting of ribs 296 within groove 265 results in driver 280 being axially fixed but rotatable in housing 250.

The second set of fingers, generally designated 300, is used to engage drive screw shaft 270 to convert driver rotation into drive screw axial motion. In injector pen 220, each finger 300 includes a base 302, a stepped portion 304, a cammable portion 306 and a tip portion 308. Base 302 of each of the two fingers 300 is located between successive fingers 293, and fingers 300 are centered 180° apart. A projecting thread segment 310 is formed on a radial inner surface of each tip portion 308 and mates with external threading 274 of drive screw shaft 270. Each thread segment 310 is positioned at a different axial position on its respective tip portion 308 such that the thread segments 310, but for the interruptions resulting from the circumferential spacing of tip portions 308, form part of a continuous helical thread with the same pitch as screw threading 274. Each thread segment 310 in axial cross-section has a ramped proximal face and a radially aligned stop face. The resilient construction of driver 280 allows fingers 300 to splay outward such that head segments 310 can axially slide over screw threading 274 when the drive screw is advanced during injecting.

Axially movable within the internal hollow of driver 280 is the follower, generally designated 320, which is injection molded as a single piece from a resilient plastic material such as acetal. Follower 320 includes a tubular, cylindrical base 322 with two slots 324 spaced 180° apart formed in its proximal end. A pair of stop ribs 328 and 330 that limit the extent of plunger motion during pen use radially project from base 322. Stop rib 328 is an annulus and completely rings base 322, and stop rib 330 is continuous except for interruptions at slots 324. During manufacturing assembly, as follower 320 is inserted distally into driver 280, a ramped, distal face portion 329 of stop rib 328 engages driver stop ribs 298 to bend fingers 293 outwardly so as to allow stop rib 328 to pass over driver stop ribs 298, at which point fingers 293 resiliently snap back inward to prevent proximal withdrawal of follower 320.

An annular flange 333 at the distal end of base 322 defines a central aperture 334 into which radially project a pair of diametrically opposed stops 336. The space within the central aperture 334 between stops 336 is large enough to accommodate drive screw shaft 270, but is not large enough to allow passage of stop head 278 at the proximal end of screw shaft 270. The abutting contact of the stops 336 by the shaft head 278 serves as an insufficient remaining dose indicator of injector pen 220.

Axially projecting from annular flange 333 is a pair of fingers, generally designated 338, which are centered 180° apart. Each finger 338 includes an upstanding base portion 340, a cammable portion 342 and a tip portion 344. Each tip portion 344 includes an inwardly projecting thread segment 346 formed on a radial inner surface and which mates with external threading 274 of drive screw shaft 270. Each thread segment 346 is positioned at a different axial position on its respective tip portion 344 to be aligned as separated pieces of a continuous helical thread. Each thread segment 346 in axial cross-section has a ramped proximal face and a radially-aligned drive face, and the resilient construction of follower 320 allows fingers 338 to splay outward as the follower is pulled proximally by plunger 360 during pen cocking as described below, such that thread segments 346 can axially slide over threading 274 of the rotatably fixed drive screw shaft 270.

Follower 320 uses its engagement with screw threading 274 to force the drive screw shaft 270 axially during injecting. Follower 320 is keyed to driver 280 to rotate therewith. In injector pen 220, this keying is achieved by each follower finger tip portion 344 closely fitting within the space between adjacent driver finger tip portions 308. In particular, tip portions 344 are dimensioned in conjunction with tip portions 308 such that when the pen injector is in the steady state arrangement shown in FIG. 13, the angular end faces of tip portions 344 and 308 are in contact. This contact helps prevent any twisting of the flex fingers while in this steady state.

The angular dimensions of base portions 340 and cammable portions 342 of the follower fingers 338, as well as the angular dimensions of the stepped portions 304 and cammable portions 306 of the driver fingers 300, are selected so as to define a slot between adjacent fingers 300 and 338 to accommodate the connecting arms of the wedge described further below.

The slots 324 of follower base 322 result in the proximal regions of base 322 serving as a pair of mounting fingers 325 that extend proximally toward plunger 360. A latching rib 350 juts radially outward from the proximal ends of each of mounting fingers 325.

A plunger, generally designated 360, is injection molded in two parts from a lightweight material such as polycarbonate. The plunger includes a tubular main body 361 and a cap 362 that friction fits over the proximate end of the main body. Plunger main body 361 includes a grip portion 364 extending distally of driver 280 which is externally accessible to be manually pulled by a user for pen cocking purposes. Along its length in the proximal direction, grip portion 364 is radially outwardly flared so as to be more readily grasped by user, such as between the thumb and fingers of a user, when pulled to the left from the perspective of a viewer of FIG. 9. Other graspable grip portion configurations may be substituted. The proximal end of plunger 360 formed by cap 362 serves as a push surface against which a force can be applied to push the plunger of a cocked pen to the right from the perspective of a viewer of FIG. 9.

The distal end of grip portion 364 is stepped down to cylindrical tube portions 366 and 368 that fit within the interior hollow of driver 280 and are slidable into and out from such hollow during use of pen 220. An inward lip 370 is formed at the distal end of tube portion 368, and four circumferentially spaced bars 372 axially project from the lip and support a plunger ring portion 374 including an interrupted, frustroconical inner surface 376. The space between ring portion 374 and lip 370 defines a recess or groove 378 around the inner circumference of plunger 360 and inward of bars 372, which groove 378 is used to connect plunger 360 with follower 320 so as to be axially fixed but rotatably free or free wheeling.

During manufacturing assembly, as follower 320 is inserted proximally into plunger 360, the engagement of latching rib 350 by inner surface 376 bends mounting fingers 325 inwardly until latching ribs 350 pass inner surface 376, at which time fingers 325 snap outward due to their resilient construction, thereby inserting latching ribs 350 within groove 378 and latching the proximal face of ring portion 374 to prevent distal withdrawal of follower 320 as plunger 360 is moved proximally. The proximal face of latching ribs 350 abut inward lip 370 to prevent over insertion of follower 320, and to cause axial motion of plunger member 360 in a distal direction to axially move follower 320 distally.

Extending within plunger 360 is a plastic stabilizing sleeve 353. Sleeve 353 may be provided to aid in preventing screw shaft 270 from radially deflecting. Sleeve 353 is shown press-fit within a collar 380 formed in cap 362, but alternatively could be mounted to follower 320.

In injector pen 220, the mechanism used to reset the drive screw when replacing a spent cartridge includes a wedge or camming element 385, a biasing member 387, and an interfacing element 389, all housed within pen housing 250. This mechanism, when the cartridge is removed, automatically without manual operation thereon by the user, disengages the threaded engagement that existed between the drive screw shaft and both the follower and driver, allowing the drive screw to be shifted proximally.

Wedge 385 includes a circular camming ring 391 with a central aperture 393 through which extends drive screw shaft 270. Camming ring 391 fits within the space between the drive screw shaft 270 and both the driver fingers 300 and the follower fingers 338. Camming ring 391 is sized sufficiently small to slide axially without contacting driver stepped portions 304 or follower base portions 340. Camming ring 391 is also sized sufficiently large to directly engage the internal coned surfaces of driver cammable portions 306 and follower cammable portions 342 when wedge 385 is slid distally from the position shown in FIG. 13, which engagement cams tip portions 308 and 344 radially outward so as to disengage thread segments 310 and 346 from drive screw threading 274.

Wedge 385 has four L-shaped connecting arms 395 that span camming ring 391 and a larger diameter, more distally located, circular outer ring 397. During axial motion of wedge 385, each connecting arm 395 slides within the slot formed between an adjacent driver stepped portion 304 and follower base portion 340. Outer ring 397 encircle and is in a spaced relationship with driver fingers 300 and follower fingers 338. The outer periphery of ring 397 is closely spaced with the pen housing shell 250 to promote concentricity with the housing.

Biasing member 387 serves to force wedge 385 axially toward a position at which the wedge cams outward the follower and driver fingers to disengage the drive screw. Biasing member 387 is shown as a coiled metal compression spring having a first end that abuts the underside of outer ring 397 radially outward of connecting arms 395, and an opposite end that abuts an acetal washer 399 that is seated on the end faces of shell inner halves 251, 252. Other known types of biasing members and materials of construction may be substituted for this metal compression spring. Washer 399 better enables spring 387 to rotate with wedge 385, which wedge is forced to rotate with driver 280 and follower 320 due to the capture of its connecting arms 395 therebetween.

Interfacing element 389 operably connects wedge 385 with the mounted fluid container, and in particular cartridge 238 in the shown configuration of injector pen 220. Interfacing element 389 includes a collar portion 400 from which depends a pair of legs 402. Each leg is bowed outward or arcuate in transverse cross section and includes a radially protruding abutment rib 404 and an axially protruding alignment rib 406 at its proximal end. When injector pen 220 is assembled, ribs 406 fit within the central opening of wedge outer ring 397 to aid in concentrically locating element 389 with wedge 385, and abutment ribs 404 contact the distal surface of outer ring 397 to transfer to wedge 385 force that is applied in the proximal direction on interfacing element 389. Ribs 408 that extend longitudinally at both sides of each leg 402 increase the strength of the legs.

Collar portion 400 includes a radially projecting annular flange 410 that centers interfacing element 389 within the internal volume of outer housing 250, as well as results in only a very small radial gap between the housing and the interfacing element. The distal face of collar portion 400 is stepped down and has a chamfered surface 412 and a cartridge-abutting surface 414. Chamfered surface 412 aids in locating the proximal end of cartridge 238 on surface 414 when injector pen 220 is assembled for use. Interfacing element 389 is prevented from falling out of housing 250 when no cartridge is present by its engagement with other parts of the pen, such as portions of the housing. For example, the interfacing element may include one or more not shown, one-way snaps that fit over and axially lock under anti-rotation tabs 259 during manufacturing insertion, which snaps, while not preventing proximal insertion, prevent the distal withdrawal of interfacing element 389 from pen housing 250 due to the abutting engagement of the snaps with the underside of tabs 259.

Figure 13:
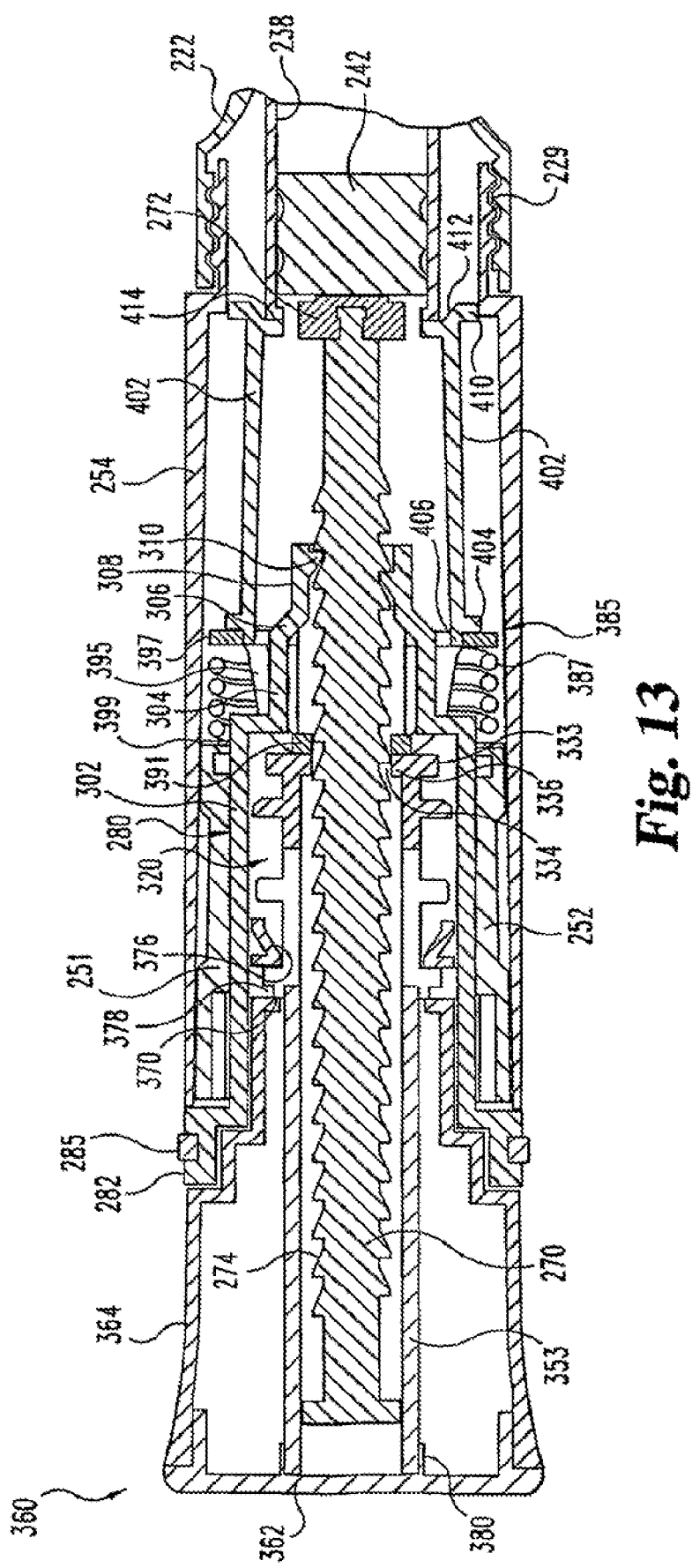
FIG. 13 is a diagrammatic cross-sectional view of proximal portions of the medication dispensing apparatus of FIG. 9 in a ready or ready-to-be-cocked state.
Figure 14:
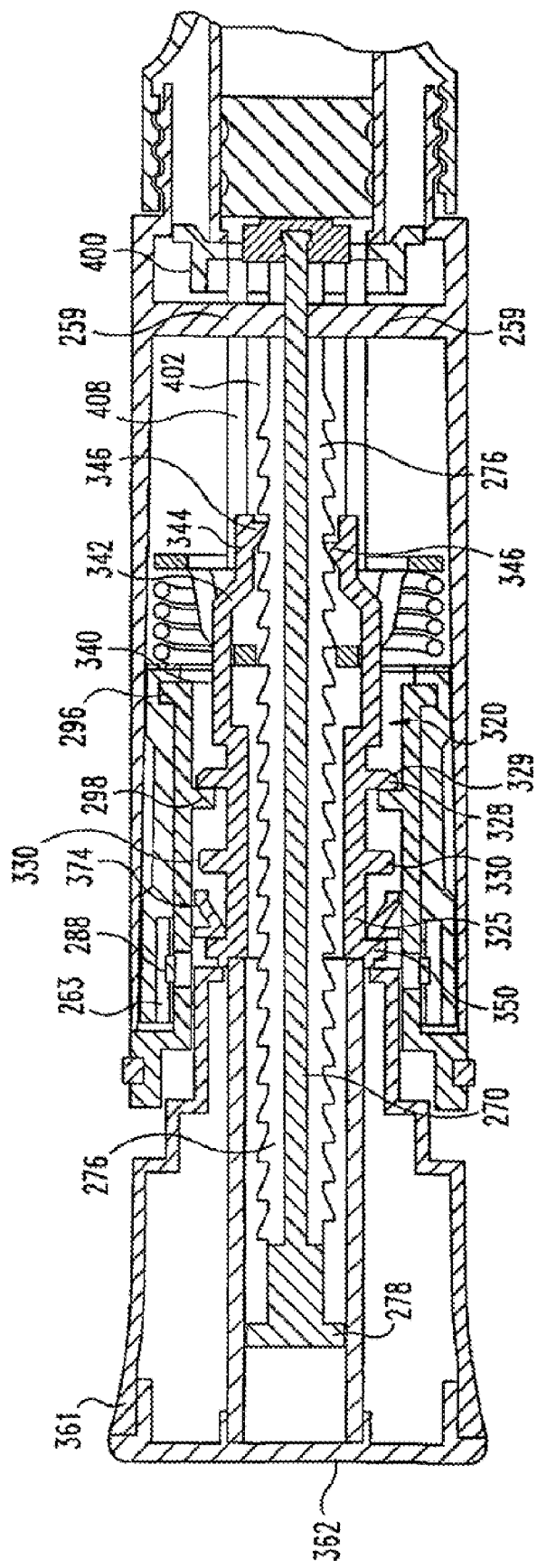
FIG. 14 is a cross-sectional view conceptually similar to the view of FIG. 13, but taken along a cut-line oriented 90° relative thereto, and after the apparatus has been manipulated from its ready-to-be-cocked state to a cocked or ready-to-inject state.
Figure 15:
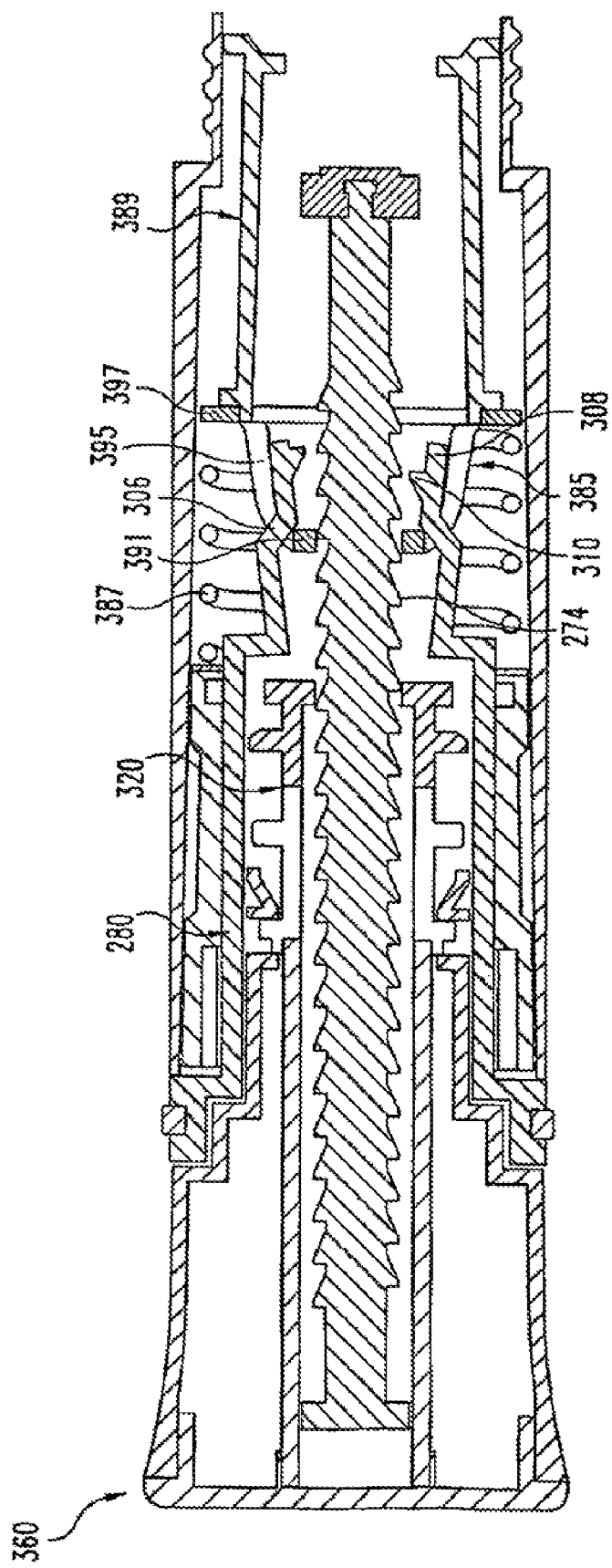
FIG. 15 is a cross-sectional view conceptually similar to the view of FIG. 13, but after the cartridge assembly has been removed for insertion of a replacement cartridge and the drive member has been reset.

The structure of injector pen 220 will be further understood in view of the following explanation of its operation given with primary reference to FIGS. 13-15. Initially, a user requiring a dose of medication will locate an injector pen 220 in the ready arrangement shown in FIG. 13.

Pen 220 is first primed in the same general manner as described above with respect to injector pen 20. After priming, pen 220 is still arranged as shown in FIG. 13 and is ready to be used for injection. By gripping grip portion 364, a user pulls plunger 360 axially away from driver 280 to cock the injector pen to deliver the dose for which it has been designed. The proximal motion of the plunger 360 is halted when the underside of follower stop rib 328, which follower is also being pulled proximally due to its connection with the plunger, abuts stop rib 298 of driver 280. During this plunger/follower proximal movement, the tip portions of follower fingers 338 flex out and slide over a thread of external threading 274. During plunger/follower proximal motion, the engagement of threading 274 with the threads 310 of driver fingers 300 prevent drive screw shaft 270 from being pulled proximally. At this point in time, pen 220 has been cocked or prepared to deliver the medicine dose it was designed to inject, and is arranged in the ready-to-inject state shown in FIG. 14.

To actually inject the medicine, after pen 220 is manipulated so the injection needle properly penetrates a user's skin, an axial, distal plunging force is applied to cap 362 to force plunger 360, and therefore follower 320, distally. As follower 320 is moved distally by plunger 360, the abutment of drive screw threading 274 by thread segments 346 causes drive screw shaft 270 to translate distally to shift cartridge piston 242 and force medication through the pen needle. During this drive screw advancement, driver tip portions 308 flex outward and slide over the passing threading 274. Plunging motion of plunger 360, and thereby advancement of drive screw shaft 270, is stopped and the medicine injection is complete, when the distal face of follower stop rib 330 directly abuts the underside of driver stop rib 298.

Pen 220 can continue to be used in the above-described manner to deliver its fixed dose until the medicine remaining in the cartridge is insufficient for a proper dosing. This insufficiency is indicated to a user by his or her inability to pull out the plunger sufficiently to cock the injector pen 220. Specifically, as plunger 360 is withdrawn proximally, follower stops 336 directly abut head 278 of drive screw shaft 270, which abutment prevents the follower thread segments 346 from entirely passing over a thread, such that when the plunger withdrawing force is removed, plunger 360 is typically drawn back into the pen housing to the ready state position shown in FIG. 13 by the resilient return of the follower fingers.

When only an insufficient dose remains, the user is able to swap out the cartridge 238 and reset the injector pen 220. Specifically, cartridge retainer 222 can be screwed off such that the cartridge and cartridge retainer are dismounted from outer shell 250, and the cartridge removed from the retainer and discarded. When cartridge 238 is so dismounted, coiled spring 387 forces wedge 385 and interfacing element 389 distally. As wedge 385 moves distally, it encounters the cammable portions 306 and 342 of the driver and follower so as to splay outward the tip portions 308 and 344. When the tip portions are so splayed out, their respective thread segments are no longer engaged with threading 274 of drive screw shaft 270, and the drive screw can be shifted proximally until the proximal face of head 278 abuts a not shown bottom stop, such as a hollow cylindrical protrusion, provided on the interior surface of plunger cap 362.

To shift the drive screw proximally, the user can then, for example, manually push back the extended drive screw 270 into the proximal portion of injector pen 220 with her finger. However, because the central hole in collar portion 400 of interfacing element 389 is smaller than the average finger, the user's finger may eventually start pushing interfacing element 389 down along with screw 270. And, when the interfacing element and thereby the camming element 385 is so pushed down a small amount, the camming outward of the flex fingers of the driver and follower ceases and the thread segments reengage with the drive screw threading 274, which reengagement may prevent the drive screw 270 from completely resetting with its head 278 against the bottom stop. Therefore, to assure a complete reset, the user may resort to using a tool, such as a pencil or perhaps a dedicated tool provided with pen 220, which fits through and does not move the interfacing element as it is used to push back the drive screw.

Figure 18:
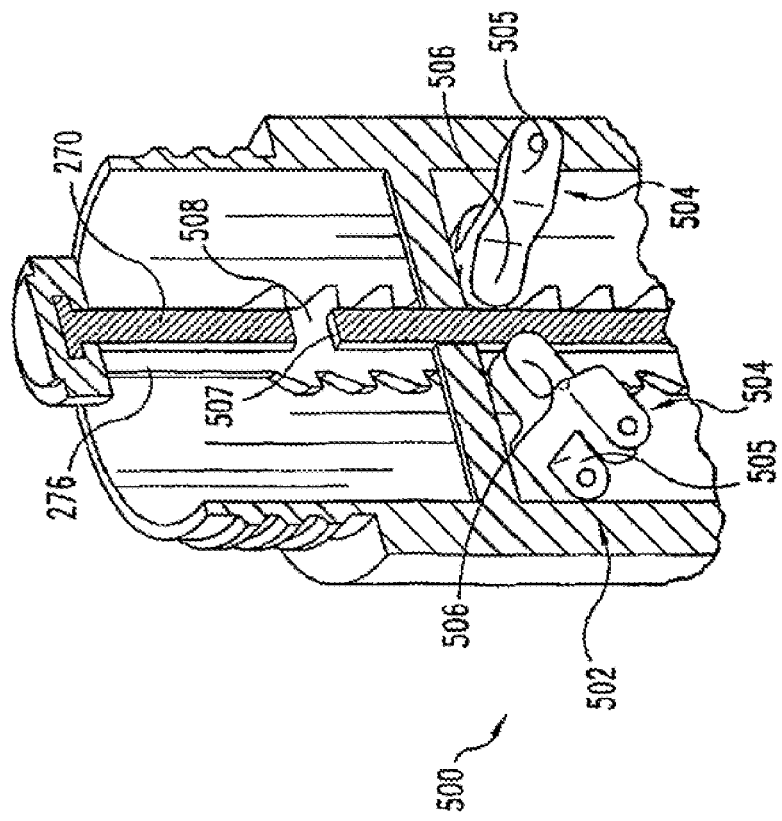
FIG. 18 is a diagrammatic, partial perspective view in cross-section of a reusable injector pen of the present invention that employs an over-center spring mechanism to assist drive screw reset.

To ensure a complete resetting of the drive screw without possibly requiring the use of a separate, external tool, the drive screw reset mechanism of the pen injector may employ an additional spring device to urge the drive screw proximally. One such device is abstractly shown in FIGS. 18 and 19, and is used in an injector pen 500 identical to injector pen 220 except for the modifications described below. The device employs at least one, and preferably two, over-center spring-loaded assemblies, generally designated 502, that work with a recess provided in the drive screw. Each assembly 502 includes a shown pivotable member 504 and a not shown biasing member that tends to force pivotable member 504 toward the arrangement shown in FIG. 19. The biasing member, which may be a known type of spring such as a torsional spring or a leaf spring, acts between member 504 and the pen housing. Pivotable member 504 has a fork portion 505 that is pivotally mounted to two not-shown projecting ears formed in shell 250 on either side of fork portion 505, and a finger portion 506 that projects from fork portion 505 and fits within a groove 276 of drive screw shaft 270. The tip of finger portion 506 is dimensioned to act against a ledge 507 formed by a recess in the screw, which in the shown embodiment is fashioned by a throughbore 508 connecting grooves 276. During use of injector pen 500, the tips of finger portions 506 slide along groove 276. When a cartridge is removed for replacement, and the follower and driver flex fingers are automatically splayed outward and the drive screw is started to be manually pushed back during reset in preparation for loading a new cartridge to pen 500, which stage of the reset is shown in FIG. 18, over-center spring loaded assemblies 502 do not interfere with or assist reset. However, when drive screw reset reaches a certain point but before the interfacing element will be pushed downward, such as when the drive screw is approximately six millimeters from the bottom of its desired travel, the tips of finger portions 506 insert within bore 508 and act proximally against the screw ledge 507, and the not shown biasing members serve to automatically snap pivot members 504 down to the arrangement shown in FIG. 19 to finish the downward travel of the drive screw for the user such that the drive screw 270 completely resets with its head against the bottom stop. Over-center spring loaded assemblies 502 thereby insure the drive screw reaches its bottom position, as well as provide a positive feedback that the drive screw has been reset properly.

In other embodiments, different elements to help ensure a complete resetting of the drive screw may be employed. Such elements include a constant force spring attached between the plunger cap and the drive screw proximal end, or a clip spring mounted to the interior of the plunger cap and which is shaped to grab and pull proximally the drive screw when the drive screw head 278 is inserted therein during screw reset.

After drive screw reset, the proximal portion of injector pen 220 is arranged as shown in FIG. 15.

Figure 19:
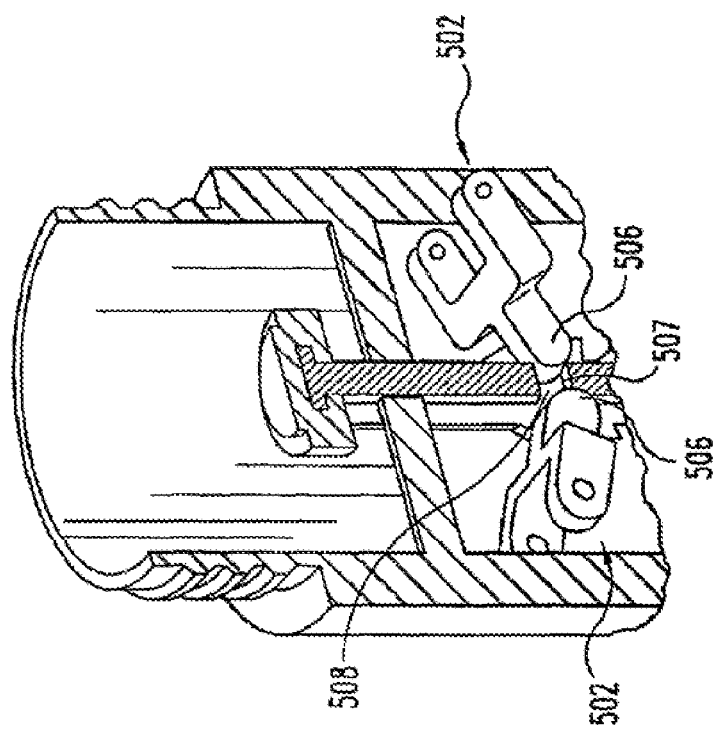
FIG. 19 is a diagrammatic, partial perspective view in cross-section of the injector pen of FIG. 18 after completion of the drive screw reset.

After a new replacement cartridge 238 is inserted into cartridge retainer 222, remounting the cartridge assembly to the pen housing results in the cartridge abutting the interfacing element 389 to force it proximally, which in turn forces wedge 385 proximally against the returning force provided by spring 387. It will be appreciated that if pen 220 includes a reset assisting device such as shown in FIGS. 18 and 19, this remounting can be used to reset the drive screw instead of the drive screw being pushed back with a user's finger, as the drive screw can be pushed back by contact with the cartridge piston as a new cartridge loaded within retainer 222 is removably mounted to shell 250 during reassembly of pen 220.

As wedge 385 moves proximally, the camming outward of the flex fingers of the driver and follower ceases and the thread segments reengage with the drive screw threading 274. After the cartridge assembly remounting, injector pen 220 can then be primed and used in the manner previously described until another new cartridge is needed, at which time the process is repeated.

It will be appreciated by the skilled artisan that injector pen 220 can be manufactured as a disposable pen merely by fixedly mounting, as opposed to removably mounting, the cartridge retainer with loaded cartridge to the pen housing. In such a disposable embodiment, the interface 389, wedge 385 and spring 387 may be eliminated as drive screw reset is not necessary.

Figure 16:
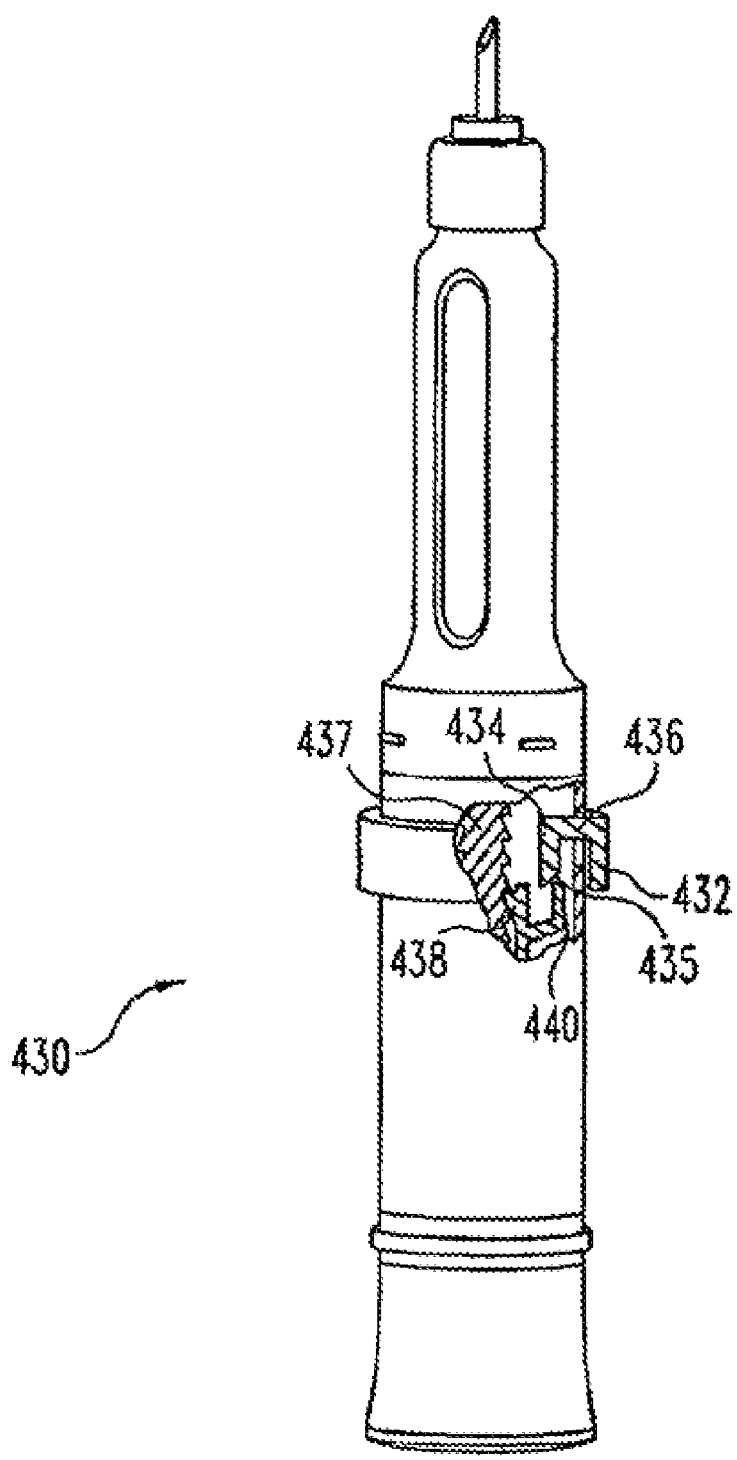
FIG. 16 is a diagrammatic front view in partial cross-section of another embodiment of a reusable injector pen of the present invention with an alternate means for resetting the drive screw.

While the mechanism shown being used in injector pen 220 to reset the drive screw is preferred, other mechanisms for resetting the drive screw may be substituted in alternate reusable devices of the present invention. For example, and as diagrammatically shown in FIG. 16, injector pen 430 includes the same working components as injector pen 220, except that it lacks wedge 385, biasing member 387 and interfacing element 389. Instead, the reset mechanism of injector pen 430 includes an externally accessible, slidable collar with an internal portion that engages cammable arms added to the drive screw engaging fingers of the driver and follower. The collar is formed in one piece with an annular grip portion 432 that is disposed around the pen housing, an annular flange 434 that resides within the pen housing internal volume, and circumferentially spaced bridges 436 spanning grip portion 432 and flange 434 which slide within slots through the pen housing. The proximal face 435 of annular flange 434 is wedge shaped. When a user wishes to reset the drive screw 437, and after the cartridge assembly has been removed to access the extended drive screw, grip portion 432 can be gripped and the collar manually pushed proximally, or down from the perspective of a FIG. 16 viewer, relative to the injector pen. When the collar is so pushed proximally, wedge face 435 engages and forces outward L-shaped camming arms that are integrally formed with and project radially outward from all of the flexible fingers of the driver and follower, such as camming arm 440 shown projecting from follower finger 438. The forcing outward of the camming arms splays their respective flex fingers radially outward to disengage the threaded segments of the flex fingers from drive screw 437, thereby allowing the drive screw to fall or be manually pushed back, or be forced back during cartridge mounting, in the proximal direction. When the proximal force on collar grip portion 432 is released, the resiliency of the driver and follower flex fingers causes the fingers to return to positions in threaded engagement with drive screw 437, which return results in the collar being forced upward to the ready position shown in FIG. 16. An additional biasing element urging the collar upward may be used in an alternate embodiment.

In another drive screw reset mechanism that functions by splaying outward the driver and follower fingers, a manually rotatable collar having an external grip portion disposed around the housing is provided. Within the pen housing, the collar includes axially depending, camming prongs that ride within tracks provided on, for example, distal end faces of the flex fingers of the driver and follower. The tracks are configured for camming action by the prongs, such that a manual twisting of the collar by the user in a first direction from a neutral angular position to a camming angular position forces the driver and follower flex fingers radially outward to disengage the threaded segments of the flex fingers from the drive screw, which can then be pushed back. When the user releases the collar, the flex fingers, due to their resilient construction, spring back to their ready positions in threaded engagement with the drive screw, thereby forcing the collar to twist from its camming position back to its neutral position.

Figure 17:
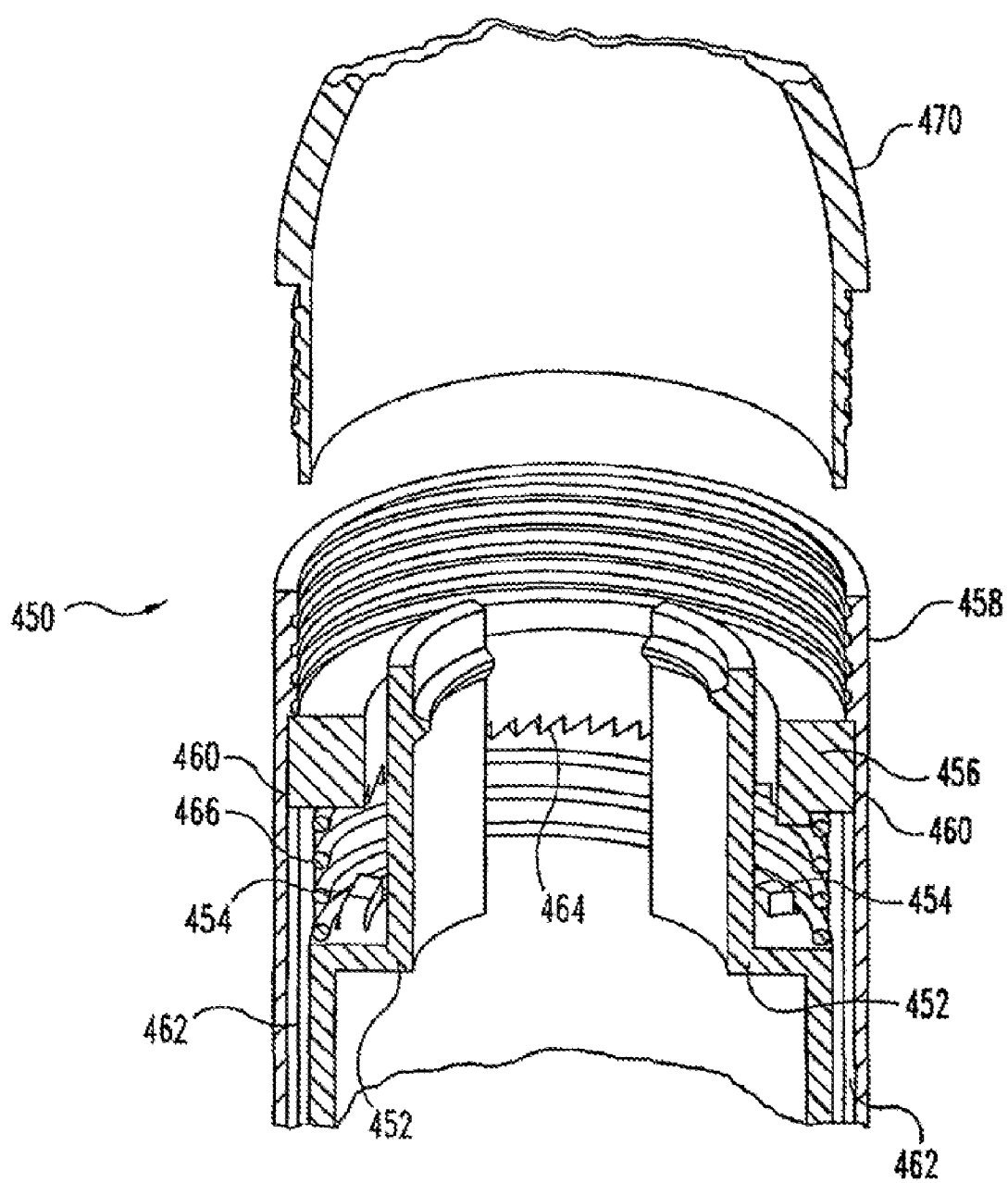
FIG. 17 is a diagrammatic perspective view in cross-section of relevant portions of another embodiment of a reusable injector pen of the present invention with an alternate drive screw reset mechanism.

In addition to the drive screw reset mechanisms of, for example, the embodiments of FIGS. 9-15 and FIG. 16 which function by disengaging the driver and follower flex fingers from the drive screw threading, other mechanism within the scope of the invention for resetting the drive screw function by permitting the flex fingers to be rotated in a reverse direction, preferably only when no medication cartridge is mounted, so as to essentially pull the drive screw back into the housing. For example, portions of an injector pen that permits such reverse rotation are diagrammatically shown in FIG. 17. The injector pen 450 of FIG. 17 is similar in most respects to pen 220, but major portions of pen 450, including but not limited to its follower and drive screw, are not shown so as to more clearly illustrate the drive screw reset mechanism. The priming driver of pen 450 includes a resilient pawl 454 formed on the distal surfaces of the base legs of the stepped portions 452 of the driver flex fingers. An annular clutch 456 is axially movable within pen outer shell 458 and is prevented from rotating therein by radially protruding keys 460 that slide within longitudinal keyways or recesses 462 within the shell. An annular arrangement of one-way clutch teeth 464 that mate with pawls 454 are located on the proximal face of clutch 456. Clutch 456 is shown being biased toward the distal or neutral position of FIG. 17 by a coiled spring 466. Although shown acting directly against driver stepped portions 452, spring 466 may be seated on a not shown, inwardly protruding shoulder of the outer shell. When the cartridge retainer 470 is mounted by being screwed down into pen housing 458, the cartridge retainer, or preferably the not shown cartridge loaded therein, abuts clutch 456 and forces it downward from the perspective of a FIG. 17 viewer against the force of a compressing spring 466. When the cartridge and retainer 470 is fully mounted, pawls 454 interface with clutch teeth 464 to prevent the driver from rotating, from the perspective of a viewer of FIG. 17, in a clockwise direction. The resiliency of each pawl 454 and the shape of its head allows the driver to be rotated in the direction which advances the not shown drive screw for priming the pen injector, during which rotation the pawls slide over the clutch teeth 464. When cartridge retainer 470 is removed to replace the spent cartridge, spring 466 forces clutch 456 distally such that teeth 464 are out of engagement with the driver pawls 454, whereby the driver can be rotated to pull the rotatably fixed drive screw proximally into the pen. In this embodiment, the driver does not need additional pawls similar to pawls 288 of injector pen 220.

The fixed dose delivered by operation of pen 20, or injector pen 220, is preset at the factory, and therefore each of these pens is particularly adapted to deliver a single dose for each complete axial withdrawal and then plunging of its respective plunger. However, each of these types of pens can be manufactured differently to achieve different, individual fixed doses. For example, by modifying during pen manufacture the pitch of threading 84 or the locations of stops ribs 120, different disposable pens 20 can each be provided with a different, individual fixed dose.

The present invention will find particularly beneficial application in delivering medicines in which the necessary dose is the preset dose of the pen, or a small multiple of that preset dose. Moreover, if delivering an excess of medicine is not medically problematic, such as in the case of a type of diabetes medicine known as glucagon like peptide-1(7-37), including analogs and derivatives thereof such as Val$^8$GLP-1 (7-37)OH, the use of the pen multiple times can introduce slightly more than the desired dose. For example, in the case of a medicine having two normal dosage amounts, such as eighteen units and fifty units, a single inventive pen adapted to dispense eighteen units for each pull/push cycle may be used to deliver both dosage amounts. Specifically, with injector pen 20, a single complete axial withdrawal and then plunging of plunger 160 can be used to deliver eighteen units, while a series of three complete axial withdrawals and then plungings of plunger 160 can be used to deliver fifty-four units, which is slightly greater than the needed fifty units.

The reusable injector pens, especially injector pen 220, described herein also may find particularly beneficial application in a medicine injecting system that utilizes a plurality of similar pens, each pen being adapted to deliver a particular fixed volume different from the fixed volumes of the other pens in the system. Such a system may use different concentrations of the same medicine provided in different disposable cartridges, with each cartridge being intended for a particular reusable pen. To reduce the likelihood of improper amounts of medicine being injected, such a system may use cartridges fixedly attached or integrated with their respective cartridge retainers, so that the cartridge/retainer is disposable as a unit when its medicine is exhausted. And, each reusable pen and its associated cartridge/retainer has a unique mounting or connecting means. For example, each model of reusable pen may have a different pitch of its threading 257, such that a disposable cartridge/retainer intended for that reusable pen would only fit that pen, and not other pens in the system. Consequently, no interchangeability of retainers/cartridges between types of reusable pens exists. Furthermore, the integrated cartridge/retainer in conjunction with the pens with the unique design of, for example, threading 257 also serve to prevent loading the reusable pens with other types of medicines available in ordinary cartridges.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

We claim:

1. A medication dispensing apparatus comprising:
   a housing;
   a fluid container mounted to said housing, said container defining a medicine-filled reservoir with a movable piston at one end and an outlet at the other end;
   a drive screw with external threading, said drive screw axially extending within said housing and movable distally to advance said movable piston toward said outlet;
   at least one anti-rotation member operably engaging said drive screw to prevent rotation of said drive screw within said housing;
   a priming driver axially retained relative to said housing and having a first portion and a second portion, said first portion internal to said housing and in threaded engagement with said drive screw, said second portion external to said housing to be manually rotatable, whereby rotation of said second portion rotates said first portion to force said drive screw to translate distally;
   a follower axially movable relative to said priming driver and rotatably fixed thereto, said follower including a portion internal to said housing and in threaded engagement with said drive screw;
   a plunger axially movable relative to said housing between a distal position and a proximal position, said plunger including a manually graspable grip portion which is pullable proximally to move said plunger from said distal position to said proximal position, said plunger connected to said follower to allow relative rotation therebetween and to shift said follower axially when said plunger moves back and forth between said distal and proximal positions; and
   wherein each of said follower portion and said priming driver first portion comprises a resilient construction, whereby when said plunger is pulled from said distal position to said proximal position to shift said follower proximally, said follower portion slides over said threading of said drive screw that is being axially retained by engagement with said priming driver first portion, and whereby when said plunger is pushed from said proximal position to said distal position to shift said follower distally, said priming driver first portion slides over said threading of said drive screw that is being axially advanced by engagement with said follower portion; and
   wherein said priming driver first portion comprises a plurality of axially extending fingers angularly spaced around a circumference of said drive screw.

2. The medication dispensing apparatus of claim 1 wherein said follower portion comprises a plurality of angularly spaced, axially extending fingers that interfit with said plurality of fingers of said priming driver first portion to rotationally key said follower with said priming driver.

3. The medication dispensing apparatus of claim 2 wherein at least one of said plurality of fingers of said priming driver first portion comprises a projecting stop that abuts at least one of said plurality of fingers of said follower portion to limit distal travel of said follower during use.

4. The medication dispensing apparatus of claim 1 wherein said priming driver comprises a radially inwardly extending ledge that abuts a radially outwardly projecting shoulder of said follower to limit proximal travel of said follower during use.

5. The medication dispensing apparatus of claim 1 wherein said priming driver comprises one of a ratchet pawl and ratchet teeth, and said housing comprises the other of the ratchet pawl and ratchet teeth, said ratchet pawl and ratchet teeth interfitting to prevent rotation of said priming driver within said housing in a direction that would force said drive screw to translate proximally.

6. The medication dispensing apparatus of claim 1 wherein said at least one anti-rotation member comprises a pair of diametrically opposed prongs that radially inwardly project from an interior wall of said housing, said prongs fitting within a pair of longitudinally extending slots formed in said threading of said drive screw.

7. The medication dispensing apparatus of claim 1 wherein said fluid container comprises a disposable cartridge removable from the apparatus for replacement, and further comprising means for resetting said drive screw to reuse the medication dispensing apparatus with a replacement cartridge.

8. The medication dispensing apparatus of claim 7 wherein said resetting means comprises a camming element movable within said housing between a ready position and a camming position, wherein movement of said camming element from said ready position to said camming position forces said follower portion and said priming driver first portion to bend radially outward to disengage said follower portion and said priming driver first portion from threaded engagement with said drive screw.

9. A medication dispensing apparatus comprising:
a housing;
a fluid container mounted to said housing, said container defining a medicine-filled reservoir with a movable piston at one end and an outlet at the other end;
a drive screw with external threading, said drive screw axially extending within said housing and movable distally to advance said movable piston toward said outlet;
at least one anti-rotation member operably engaging said drive screw to prevent rotation of said drive screw within said housing;
a priming driver axially retained relative to said housing and having a first portion and a second portion, said first portion internal to said housing and in threaded engagement with said drive screw, said second portion external to said housing to be manually rotatable, whereby rotation of said second portion rotates said first portion to force said drive screw to translate distally;
a follower axially movable relative to said priming driver and rotatably fixed thereto, said follower including a portion internal to said housing and in threaded engagement with said drive screw;
a plunger axially movable relative to said housing between a distal position and a proximal position, said plunger including a manually graspable grip portion which is pullable proximally to move said plunger from said distal position to said proximal position, said plunger connected to said follower to allow relative rotation therebetween and to shift said follower axially when said plunger moves back and forth between said distal and proximal positions; and
wherein each of said follower portion and said priming driver first portion comprises a resilient construction, whereby when said plunger is pulled from said distal position to said proximal position to shift said follower proximally, said follower portion slides over said threading of said drive screw that is being axially retained by engagement with said priming driver first portion, and whereby when said plunger is pushed from said proximal position to said distal position to shift said follower distally, said priming driver first portion slides over said threading of said drive screw that is being axially advanced by engagement with said follower portion;
wherein said fluid container comprises a disposable cartridge removable from the apparatus for replacement, and further comprising means for resetting said drive screw to reuse the medication dispensing apparatus with a replacement cartridge;
wherein said resetting means comprises a camming element movable within said housing between a ready position and a camming position, wherein movement of said camming element from said ready position to said camming position forces said follower portion and said priming driver first portion to bend radially outward to disengage said follower portion and said priming driver first portion from threaded engagement with said drive screw; and
wherein said camming element comprises an inner ring, an outer ring and a plurality of arms connecting said inner ring and said outer ring, said inner ring positioned radially between said drive screw and both said follower portion and said priming driver first portion, said outer ring positioned within said housing radially outward of said follower portion and said priming driver first portion, and said connecting arms extending through angular gaps between said follower portion and said priming driver first portion.

10. The medication dispensing apparatus of claim 9 wherein said outer ring is located distally of said inner ring.

11. A medication dispensing apparatus comprising:
a housing;
a fluid container mounted to said housing, said container defining a medicine-filled reservoir with a movable piston at one end and an outlet at the other end;
a drive screw with external threading, said drive screw axially extending within said housing and movable distally to advance said movable piston toward said outlet;
at least one anti-rotation member operably engaging said drive screw to prevent rotation of said drive screw within said housing;
a priming driver axially retained relative to said housing and having a first portion and a second portion, said first portion internal to said housing and in threaded engagement with said drive screw, said second portion external to said housing to be manually rotatable, whereby rotation of said second portion rotates said first portion to force said drive screw to translate distally;
a follower axially movable relative to said priming driver and rotatably fixed thereto, said follower including a portion internal to said housing and in threaded engagement with said drive screw;
a plunger axially movable relative to said housing between a distal position and a proximal position, said plunger including a manually graspable grip portion which is pullable proximally to move said plunger from said distal position to said proximal position, said plunger connected to said follower to allow relative rotation therebetween and to shift said follower axially when said plunger moves back and forth between said distal and proximal positions; and
wherein each of said follower portion and said priming driver first portion comprises a resilient construction, whereby when said plunger is pulled from said distal position to said proximal position to shift said follower proximally, said follower portion slides over said threading of said drive screw that is being axially retained by engagement with said priming driver first portion, and whereby when said plunger is pushed from said proximal position to said distal position to shift said follower distally, said priming driver first portion slides over said threading of said drive screw that is being axially advanced by engagement with said follower portion;

wherein said fluid container comprises a disposable cartridge removable from the apparatus for replacement, and further comprising means for resetting said drive screw to reuse the medication dispensing apparatus with a replacement cartridge;

wherein said resetting means comprises a camming element movable within said housing between a ready position and a camming position, wherein movement of said camming element from said ready position to said camming position forces said follower portion and said priming driver first portion to bend radially outward to disengage said follower portion and said priming driver first portion from threaded engagement with said drive screw; and a biasing member urging said camming element from said ready position to said camming position, and wherein said camming element is operably connectable to said fluid container such that mounting of said fluid container to said housing automatically shifts said camming element from said camming position to said ready position against the urging of said biasing member, and such that dismounting said fluid container from said housing allows said biasing member to automatically shift said camming element from said ready position to said camming position.

12. The medication dispensing apparatus of claim 11 wherein said camming element is operably connectable to said fluid container by a separate interface member disposed within said housing distally of said camming element, said interface member comprising a cartridge abutting surface and a camming element abutting surface.

13. A medication dispensing apparatus comprising:
a housing;
a fluid container mounted to said housing, said container defining a medicine-filled reservoir with a movable piston at one end and an outlet at the other end;
a drive screw with external threading, said drive screw axially extending within said housing and movable distally to advance said movable piston toward said outlet;
at least one anti-rotation member operably engaging said drive screw to prevent rotation of said drive screw within said housing;
a priming driver axially retained relative to said housing and having a first portion and a second portion, said first portion internal to said housing and in threaded engagement with said drive screw, said second portion external to said housing to be manually rotatable, whereby rotation of said second portion rotates said first portion to force said drive screw to translate distally;
a follower axially movable relative to said priming driver and rotatably fixed thereto, said follower including a portion internal to said housing and in threaded engagement with said drive screw;
a plunger axially movable relative to said housing between a distal position and a proximal position, said plunger including a manually graspable grip portion which is pullable proximally to move said plunger from said distal position to said proximal position, said plunger connected to said follower to allow relative rotation therebetween and to shift said follower axially when said plunger moves back and forth between said distal and proximal positions; and
wherein each of said follower portion and said priming driver first portion comprises a resilient construction, whereby when said plunger is pulled from said distal position to said proximal position to shift said follower proximally, said follower portion slides over said threading of said drive screw that is being axially retained by engagement with said priming driver first portion, and whereby when said plunger is pushed from said proximal position to said distal position to shift said follower distally, said priming driver first portion slides over said threading of said drive screw that is being axially advanced by engagement with said follower portion;

wherein said fluid container comprises a disposable cartridge removable from the apparatus for replacement, and further comprising means for resetting said drive screw to reuse the medication dispensing apparatus with a replacement cartridge;

wherein said resetting means comprises a camming element movable within said housing between a ready position and a camming position, wherein movement of said camming element from said ready position to said camming position forces said follower portion and said priming driver first portion to bend radially outward to disengage said follower portion and said priming driver first portion from threaded engagement with said drive screw; and wherein said camming element comprises a grip portion and a camming portion, said grip portion external to said housing and connected to said camming portion internal to said housing.

14. The medication dispensing apparatus of claim 13 wherein said camming element translates axially when shifted from said ready position to said camming position.

15. The medication dispensing apparatus of claim 7 further comprising means for ensuring a complete resetting of said drive screw.

16. A medication dispensing apparatus comprising:
a housing;
a fluid container mounted to said housing, said container defining a medicine-filled reservoir with a movable piston at one end and an outlet at the other end;
a drive screw with external threading, said drive screw axially extending within said housing and movable distally to advance said movable piston toward said outlet;
at least one anti-rotation member operably engaging said drive screw to prevent rotation of said drive screw within said housing;
a priming driver axially retained relative to said housing and having a first portion and a second portion, said first portion internal to said housing and in threaded engagement with said drive screw, said second portion external to said housing to be manually rotatable, whereby rotation of said second portion rotates said first portion to force said drive screw to translate distally;
a follower axially movable relative to said priming driver and rotatably fixed thereto, said follower including a portion internal to said housing and in threaded engagement with said drive screw;
a plunger axially movable relative to said housing between a distal position and a proximal position, said plunger including a manually graspable grip portion which is pullable proximally to move said plunger from said distal position to said proximal position, said plunger connected to said follower to allow relative rotation therebetween and to shift said follower axially when said plunger moves back and forth between said distal and proximal positions;
wherein each of said follower portion and said priming driver first portion comprises a resilient construction, whereby when said plunger is pulled from said distal position to said proximal position to shift said follower proximally, said follower portion slides over said threading of said drive screw that is being axially retained by engagement with said priming driver first portion, and whereby when said plunger is pushed from said proximal position to said distal position to shift said follower distally, said priming driver first portion slides over said threading of said drive screw that is being axially advanced by engagement with said follower portion;

wherein said fluid container comprises a disposable cartridge removable from the apparatus for replacement, and further comprising means for resetting said drive screw to reuse the medication dispensing apparatus with a replacement cartridge; and means for ensuring a complete resetting of said drive screw, wherein said resetting ensuring means comprises at least one over-center spring mechanism engagable with said drive screw.

17. The medication dispensing apparatus of claim 16 wherein said at least one over-center spring mechanism comprises at least one spring loaded pivotable member including a tip portion that slides within a longitudinally extending slot formed in said threading of said drive screw, and wherein said pivotable member automatically pivots from a first position to a second position when said tip portion inserts within a recess formed in said slot and acts against a ledge surface of said drive screw which defines said recess.

18. The medication dispensing apparatus of claim 17 wherein said ledge surface comprises a surface defining a throughbore through said drive screw.

19. The medication dispensing apparatus of claim 17 wherein said at least one spring loaded pivotable member comprises first and second pivotable members each including a tip portion that slides within a different longitudinally extending slot formed in said threading of said drive screw.

* * * * *